United States Patent
Su et al.

(10) Patent No.: US 8,703,951 B2
(45) Date of Patent: Apr. 22, 2014

(54) SYNTHESIS OF 4H-BENZO[D]PYRROLO[1,2-A]THIAZOLES AND INDOLIZINO[6,7-B]INDOLE DERIVATIVES AND THEIR USE AS ANTITUMOR THERAPEUTIC AGENTS

(75) Inventors: Tsann-Long Su, New Taipei (TW); Ting-Chao Chou, Paramus, NJ (US); Te-Chang Lee, Taipei (TW)

(73) Assignee: Academia Sinica, Taipei (TW)

( * ) Notice: Subject to any disclaimer, the term of this patent is extended or adjusted under 35 U.S.C. 154(b) by 18 days.

(21) Appl. No.: 13/549,572

(22) Filed: Jul. 16, 2012

(65) Prior Publication Data

US 2013/0178629 A1    Jul. 11, 2013

Related U.S. Application Data

(60) Provisional application No. 61/508,145, filed on Jul. 15, 2011.

(51) Int. Cl.
| | | |
|---|---|---|
| C07D 471/00 | (2006.01) | |
| C07D 491/00 | (2006.01) | |
| C07D 498/00 | (2006.01) | |
| C07D 513/00 | (2006.01) | |
| C07D 515/00 | (2006.01) | |
| C07D 487/00 | (2006.01) | |
| C07D 495/00 | (2006.01) | |
| C07D 497/00 | (2006.01) | |

(52) U.S. Cl.
USPC ............................................. 546/70; 548/421

(58) Field of Classification Search
CPC .. C07D 471/00; C07D 491/00; C07D 498/00; C07D 513/00; C07D 515/00
See application file for complete search history.

(56) References Cited

U.S. PATENT DOCUMENTS 6,838,456 B2 * 1/2005 Orme et al. ................. 514/233.2

* cited by examiner

*Primary Examiner* — Rita Desai
*Assistant Examiner* — Ben S Michelson
(74) *Attorney, Agent, or Firm* — VLP Law Group LLP

(57) ABSTRACT

The present invention provides a series of 2,3-bis(hydroxymethyl)-4H-benzo[d]pyrrolo-[1,2-a]thiazoles and 1,2-bis(hydroxymethyl)indolizino[6,7-b]indole derivatives and their bis(alkylcarbamates) derivatives. These derivatives were designed as bi-functional DNA cross-linking agents. The in vitro cytotoxicity study of these compounds revealed that they exhibit significant anti-proliferative activity in inhibiting human lymphoblastic leukemia and various solid tumor cell growth. The compounds also exhibit therapeutic efficacy against human breast carcinoma and lung cancer in xenograft model. The compounds generally possess potent antitumor activity to kill various human solid tumors and have high potential for clinical applications.

8 Claims, 12 Drawing Sheets

Scheme 1. The proposed mechanism of action of DNA cross-linking by 2,3-bis(hydroxymethyl)-4H-benzo[d]pyrrolo-[1,2-a]thiazoles and their bis(alkylcarbamates)

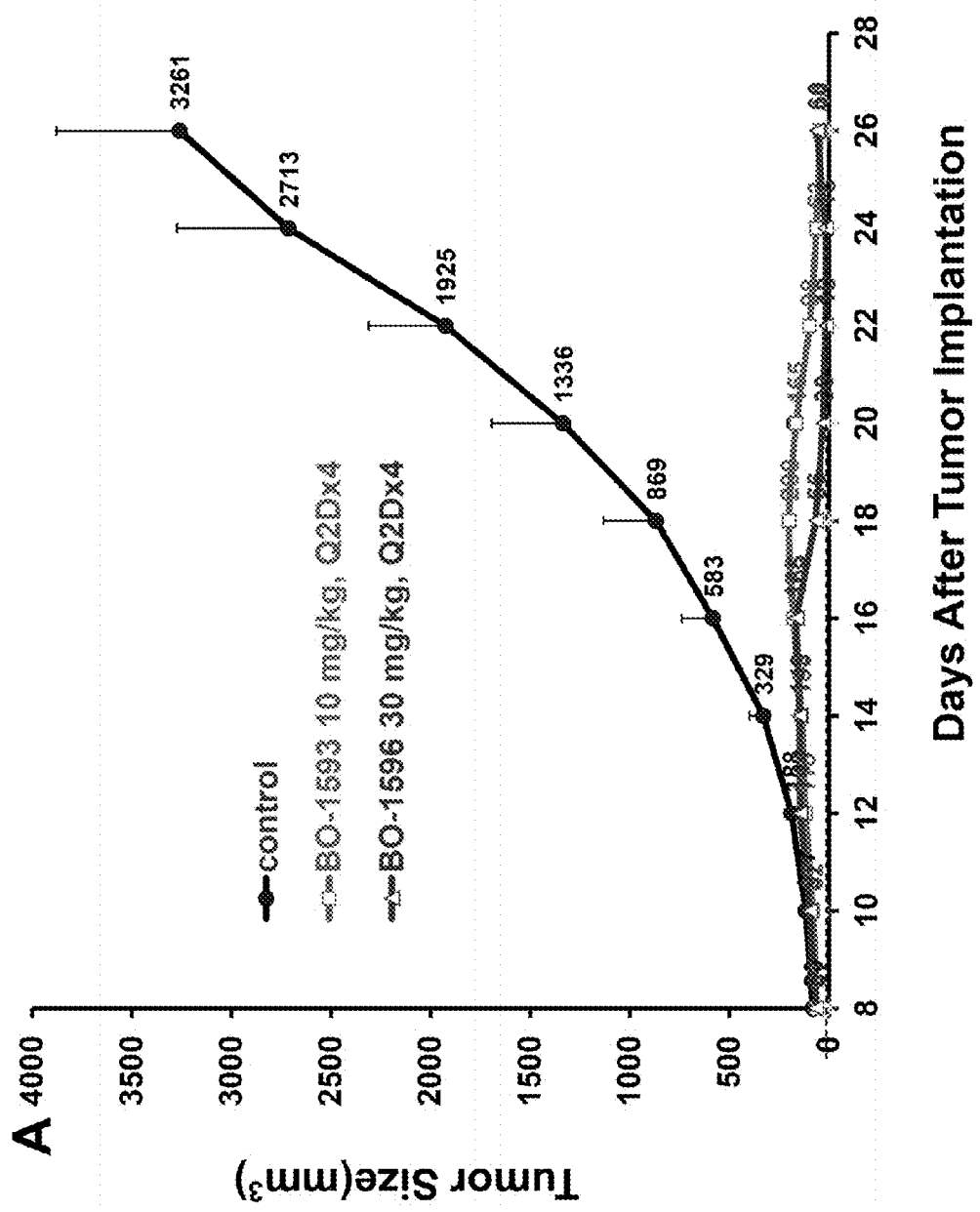

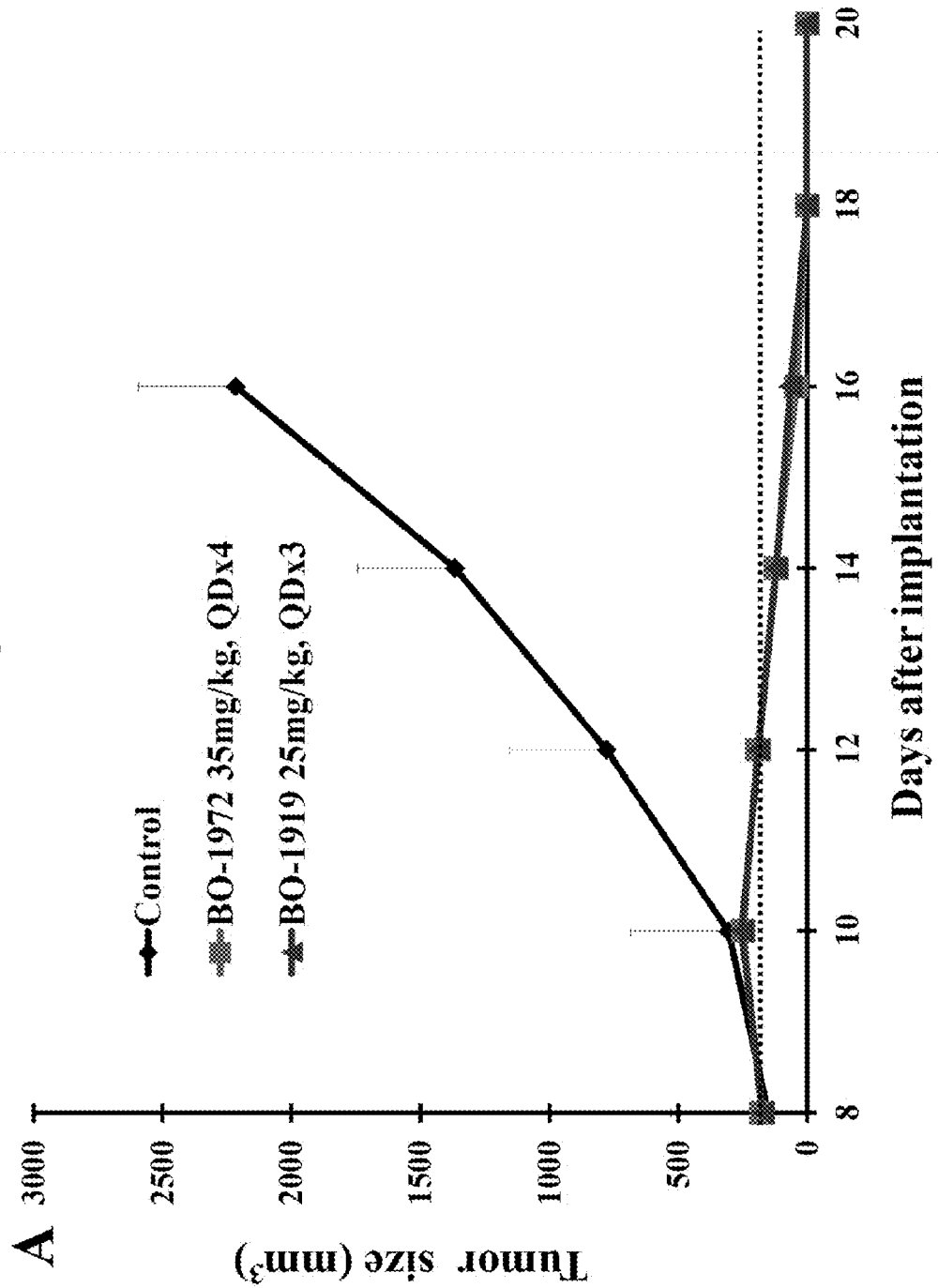

SYNTHESIS OF 4H-BENZO[D]PYRROLO[1,2-A]THIAZOLES AND INDOLIZINO[6,7-B]INDOLE DERIVATIVES AND THEIR USE AS ANTITUMOR THERAPEUTIC AGENTS

RELATED APPLICATIONS

This application claims priority from U.S. Provisional Patent Application Ser. No. 61/508,145 which was filed on Jul. 15, 2011, the contents of which is incorporated by reference.

BACKGROUND OF THE INVENTION

1. Field of the Invention

The present invention relates to new 2,3-bis(hydroxymethyl)-4H-benzo[d]pyrrolo-[1,2-alpha]thiazoles and 1,2-bis (hydroxymethyl)indolizino[6,7-beta]indole derivatives and their bis(alkylcarbamates) derivatives. These derivatives were designed as bi-functional DNA cross-linking agents, and exhibit significant anti-proliferative activity in inhibiting various cancers including human lymphoblastic leukemia, various solid tumor cell growth, human breast carcinoma, and lung cancer.

2. Description of the Related Art

DNA bifunctional alkylating agents, such as thioimidazoles (i.e., carmethizole, 1, FIG. 1),[1] bis(hydroxymethyl)pyrrolidine derivatives (i.e., $2^2$ and $3^3$) and 2,3-dihydroxy-6,7-bis(hydroxylmethyl)pyrrolizines [e.g., 4 (IPP)],[4] were developed originally from the pyrrolizine alkaloid (5). These agents are able to induce DNA interstrand or intrastrand cross-linking by a mechanism similar to that of mitomycin C derivatives (6, MMCs).[3] Unlike MMCs, the DNA cross-linking induced by pyrrolizines does not require the reductive reactivation by reductase. The plausible mechanism of action for DNA interstrand or intrastrand cross-linking induced by bis(carbamoyloxymethyl)pyrroles or pyrrolizines is probably via a $S_N1$ electrophilic reaction.[3] Thus, the potential electrophilic reactivity of these agents (the hydroxyl groups or carbamoyl moieties are leaving group in an alkyl-oxygen cleavage mechanism) would be modulated by the degree of electronic perturbation in participating of the pyrrole. Structure-activity relationship (SAR) studies demonstrated that the lipophilicity, planarity, size and the electron properties of the substituent(s) on the C-atom adjunct to the heterocyclic N-atom may also affect their antitumor activity.[5] Of bis(hydroxymethyl)pyrrolidine analogues, compound 10 was found to have significant antitumor activity against a broad range of experimental human tumor xenografts.[6] phenylpyrrolizines may also affect their antitumor activity.[5] Anderson et al. further synthesized bis(carbamoylmethyl) derivatives of pyrrolo [2,1-a]isoquinoline (13 and 14, FIG. 2), which bear angular tricyclic structures to limit the deviation from co-planarity of the phenyl and pyrrolo rings.[5] The results showed that these agents exhibited a broad spectrum of antitumor activity against a wide range of tumors.

In our study of bifunctional alkylating agents as potential antitumor agents, we have recently synthesized a series of bis(hydroxymethyl)-8H-3a-azacyclopenta-[α]indene-1-yl and their bis(methylcarbamate) derivatives, which can considered as "benzologue" derivatives of pyrrolizines (4).[7] We reported that these agents exhibited significant cytotoxicity in inhibiting human lymphoblastic leukemia and a variety of human tumor cell growth in vitro and have potent therapeutic efficacy in tumor xenograft model. Among these agents, complete tumor remission (CR) in nude mice bearing human breast carcinoma MX-1 xenograft was observed when mice were treated with bis(hydroxymethyl) derivatives, BO-1090 (7, FIG. 2) and BO-1099 (8). Moreover, more than 95% of tumor suppression was achieved when mice bearing human prostate aderonamacarcinoma PC3 xenograft were treated with the bis(methylcarbamates) derivatives, BO-1012 (9) and BO-1124 (10). Remarkably, we found that the combination treatment of BO-1012 (9) with arsenic trioxide (ATO, DNA repair inhibitor) resulted in more than 82% tumor suppression in nude mice bearing human large cell lung carcinoma H460 xenograft and cisplatin-resistant NTUB 1/P human bladder carcinoma xenografts (>92% suppression) in xenograft model.[8] More recently, we have synthesized a series of linear 5,10-dihydropyrrolo[1,2-b]isoquinolines and their bis(alkylcarbamates). Of these derivatives, BO-1107 (11) was shown to have potent antitumor activity against human breast carcinoma MX-1 and ovarian adenocarcinoma SK-OV-3 xenografts.[9]

Earlier report on the study of the mechanism of action of thioimidazoles (e.g. 1, FIG. 1) or dihydropyrrolo[2,1-b]thiazole (12, FIG. 2)[10] suggested that the sulfur atom participates in the expulsion of the hydroxyl or carbamate moiety leading to the nucleophilic attack by DNA.[11] Utilizing the known benzo[d]pyrrolo[1,2-a]thiazole diesters,[12,13] one can prepare 2,3-bis(hydroxymethyl)-4H-benzo[d]pyrrolo[1,2-a]thiazoles and their bis(alkylcarbamate) derivatives (13), which can be considered as a "benzologue" of compound 12 for antitumor evaluation. A plausible mechanism of action for DNA cross-linking induced by compound 13 is proposed in Scheme 1 as shown in FIG. 3.

Additionally, it was reported that the naturally occurring β-carboline alkaloids and the synthetic indole alkaloids, which possess a common tricyclic 9H-pyrido[3,4-b]indole ring system, also possess potent antitumor activities.[14,15] This suggested that β-carboline alkaloids are able to intercalate into the double strands of DNA. Consequently, it is of great interest to apply the tricyclic 9H-pyrido[3,4-b]indole ring system for constructing the new bi-functional DNA alkylating agents, namely 1,2-bis(hydroxymethyl)indolizino[6,7-b]indole derivatives (14, FIG. 2).

SUMMARY OF THE INVENTION

The present invention provides novel derivatives that are able to induce DNA cross-linking by the same mechanism as that of 5,10-dihydropyrrolo[1,2-b]isoquinolines (11) and exhibit potent antitumor activities. Based on our hypothesis, we synthesized a series of 2,3-bis-(hydroxymethyl)-4H-benzo[d]pyrrolo-[1,2-c]thiazoles (13) and 1,2-bis(hydroxylmethyl)-indolizino[6,7-b]indole derivatives (14) and their bis (alkylcarbamates) for antitumor evaluation. Our studies revealed that these agents (13 and 14) exhibited potent antitumor activity both in vitro and in xenograft model against a variety of human tumors. The present invention, therefore, provide newly synthesized compounds and their application for use as potential antitumor agents, and more specifically for the treatment of human lymphoblastic leukemia and various solid tumor cell growth, human breast carcinoma and lung cancer.

The present inventors synthesized a series of bis(hydroxymethyl) of 4H-benzo[d]pyrrolo[1,2-a]thiazoles and indolizino[6,7-b]indole derivatives (Formula I and III, respectively) and their corresponding bis(carbamates) (Formula II and IV, respectively).

Exemplary compounds disclosed herein are shown below, compounds of Formula I (Table 1), Formula II (Table 2), Formula III (Table 3), and Formula IV (Table 4).

TABLE 1

The yields and melting points (mp) of benzo[d]pyrrolo[2,1-b]thiazole-2,3-diyl)dimethanol (5a-j)

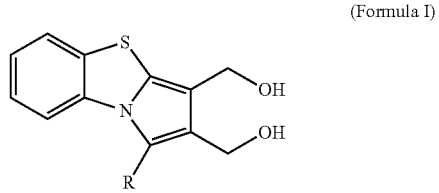

(Formula I)

| Compd. No. | BO No. | R | Yield (%) | mp (° C.) |
|---|---|---|---|---|
| 18a | 1595 | Me | 82 | 138-139 |
| 18b | 1592 | 4'-F—$C_6H_4$ | 76 | 155-156 |
| 18c | 1582 | 4'-Cl—$C_6H_4$ | 88 | 151-152 |
| 18d | 1601 | 3',4'-F—$C_6H_3$ | 83 | 154-155 |
| 18e | 1710 | 3',4'-Cl—$C_6H_3$ | 84 | 159-160 |
| 18f | 1719 | 3'-Cl-4'-F—$C_6H_3$ | 75 | 178-179 |
| 18g | 1646 | 4'-MeO—$C_6H_4$ | 91 | 156-157 |
| 18h | 1724 | 3',4'-di-MeO—$C_6H_3$ | 91 | 215-216 |
| 18i | 1715 | 3',4',5'-tri-MeO—$C_6H_2$ | 74 | 160-161 |
| 18j | 1727 | Cyclopropane | 67 | 153-154 |

TABLE 2

The yields and melting points (mp) of benzo[d]pyrrolo[2,1-b]thiazole-2,3-diyl)bis(methylene) bis(alkylcarbamate)

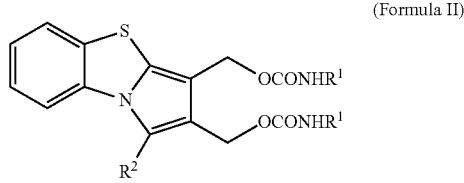

(Formula II)

| Compd. No. | BO No. | $R^1$ | $R^2$ | Yield (%) | mp (° C.) |
|---|---|---|---|---|---|
| 19a | 1653 | Et | Me | 85 | 158-159 |
| 19b | 1593 | Et | 4'-F—$C_6H_4$ | 79 | 172-173 |
| 19c | 1596 | Et | 4'-Cl—$C_6H_4$ | 78 | 190-191 |
| 19d | 1602 | Et | 3',4'-F—$C_6H_3$ | 85 | 167-168 |
| 19e | 1713 | Et | 3',4'-Cl—$C_6H_3$ | 90 | 178-179 |
| 19f | 1721 | Et | 3'-Cl-4'-F—$C_6H_3$ | 82 | 158-159 |
| 19g | 1647 | Et | 4'-MeO—$C_6H_4$ | 85 | 146-147 |
| 19h | 1725 | Et | 3',4'-di-MeO—$C_6H_3$ | 90 | 145-146 |
| 19i | 1716 | Et | 3',4',5'-tri-MeO—$C_6H_2$ | 89 | 196-197 |
| 19j | 1728 | Et | Cyclopropane | 75 | 187-188 |
| 20a | 1652 | i-Pr | Me | 85 | 158-159 |
| 20b | 1597 | i-Pr | 4'-F—$C_6H_4$ | 79 | 172-173 |
| 20c | 1600 | i-Pr | 4'-Cl—$C_6H_4$ | 78 | 190-191 |
| 20d | 1635 | i-Pr | 3',4'-F—$C_6H_3$ | 85 | 167-168 |
| 20e | 1714 | i-Pr | 3',4'-Cl—$C_6H_3$ | 90 | 178-179 |
| 20f | 1720 | i-Pr | 3'-Cl-4'-F—$C_6H_3$ | 82 | 158-159 |
| 20g | 1648 | i-Pr | 4'-MeO—$C_6H_4$ | 85 | 146-147 |
| 20h | 1726 | i-Pr | 3',4'-di-MeO—$C_6H_3$ | 90 | 145-146 |
| 20i | 1717 | i-Pr | 3',4',5'-tri-MeO—$C_6H_2$ | 89 | 196-197 |
| 20j | 1729 | i-Pr | Cyclopropane | 75 | 187-188 |

TABLE 3

The yields and melting points (mp) of 6-methyl-6,11-dihydro-5H-indolizino[6,7-b]-indole-1,2-diyl)dimethanol derivatives

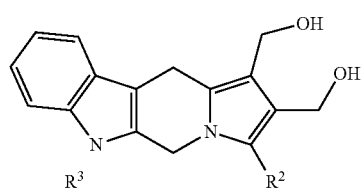

(Formula III)

| Comp. No. | BO No. | Substitute $R^2$ | $R^3$ | Yield % | mp ° C. |
|---|---|---|---|---|---|
| 33a | 1922 | Me | Me | 79 | 200-201 |
| 33b | 1972 | Me | Et | 80 | 216-217 |
| 33c | 1950 | Me | $C_6H_5CH_2$ | 81 | 253-254 |
| 26a | 1978 | Et | Me | 66 | 193-194 |
| 26b | 1940 | $C_6H_5$ | Me | 82 | 122-123 |
| 26c | 1917 | 4'-F—$C_6H_4$ | Me | 78 | 240-241 |
| 26d | 1934 | 4'-Cl—$C_6H_4$ | Me | 77 | 238-239 |
| 26e | 1946 | 3',4'-di-F—$C_6H_3$ | Me | 79 | 195-196 |
| 26f | 1964 | 3'-Cl-4'-F—$C_6H_3$ | Me | 76 | 202-203 |
| 26g | 1931 | 4'-MeO—$C_6H_4$ | Me | 79 | 220-221 |
| 26h | 1967 | 3,4-di-MeO—$C_6H_3$ | Me | 79 | 156-157 |
| 26i | 1975 | 3',4',5'-tri-MeO—$C_6H_2$ | Me | 76 | 177-178 |

TABLE 4

The yields and melting points (mp) of 6-methyl-6,11-dihydro-5H-indolizino[6,7-b]indole-1,2-diyl]bis(methylene) bis(alkylcarbamate) derivatives

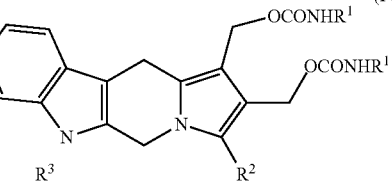

(Formula IV)

| Comp. No. | BO No. | $R^1$ | Substitute $R^2$ | $R^3$ | Yield % | mp ° C. |
|---|---|---|---|---|---|---|
| 34a | 1923 | Et | Me | Me | 69 | 165-166 |
| 34b | 1973 | Et | Me | Et | 57 | 178-179 |
| 34c | 1951 | Et | Me | $C_6H_5CH_2$ | 59 | 204-205 |
| 27a | 1979 | Et | Et | Me | 79 | 212-213 |
| 27b | 1941 | Et | $C_6H_5$ | Me | 64 | 202-203 |
| 27c | 1918 | Et | 4'-F—$C_6H_4$ | Me | 73 | 168-169 |
| 27d | 1935 | Et | 4'-Cl—$C_6H_4$ | Me | 58 | 176-177 |
| 27e | 1947 | Et | 3',4'-di-F—$C_6H_3$ | Me | 58 | 196-197 |
| 27f | 1965 | Et | 3'-Cl-4'-F—$C_6H_3$ | Me | 58 | 194-195 |
| 27g | 1932 | Et | 4'-MeO—$C_6H_4$ | Me | 75 | 116-117 |
| 27h | 1968 | Et | 3',4'-di-MeO—$C_6H_3$ | Me | 54 | 153-154 |
| 27i | 1976 | Et | 3',4',5'-tri-MeO—$C_6H_2$ | Me | 59 | 203-204 |
| 35a | 1924 | i-Pr | Me | Me | 68 | 190-191 |
| 35b | 1974 | i-Pr | Me | Et | 63 | 219-220 |
| 35c | 1952 | i-Pr | Me | $C_6H_5CH_2$ | 66 | 222-223 |
| 28a | 1980 | i-Pr | Et | Me | 68 | 200-201 |
| 28b | 1942 | i-Pr | $C_6H_5$ | Me | 64 | 165-166 |
| 28c | 1919 | i-Pr | 4'-F—$C_6H_4$ | Me | 64 | 195-196 |
| 28d | 1936 | i-Pr | 4'-Cl—$C_6H_4$ | Me | 60 | 195-196 |
| 28e | 1948 | i-Pr | 3',4'-di-F—$C_6H_3$ | Me | 71 | 211-212 |
| 28f | 1966 | i-Pr | 3'-Cl-4'-F—$C_6H_3$ | Me | 68 | 235-236 |
| 28g | 1933 | i-Pr | 4'-MeO—$C_6H_4$ | Me | 75 | 179-180 |
| 28h | 1969 | i-Pr | 3,4-di-MeO—$C_6H_3$ | Me | 61 | 207-208 |
| 28i | 1977 | i-Pr | 3',4',5'-tri-MeO—$C_6H_2$ | Me | 70 | 205-206 |

These agents were subjected to antitumor studies. The results revealed that these compounds exhibit significant cytotoxicity in inhibiting various human tumor cell growth in vitro and could possess potent therapeutic efficacy in animal bearing human tumor xenografts (such as human breast carcinoma MX-1 and lung carcinoma HCT-116). The results demonstrated that these compounds could possess potent antitumor therapeutic efficacy and have potential for clinical applications.

In one aspect, the present application discloses compounds of Formula I:

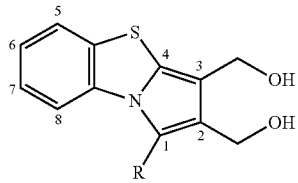

Formula I wherein:

R is hydrogen, a $C_1$-$C_5$ linear, branched or cyclic alkyl group, an aryl or a benzyl, which may be unsubstituted or substituted;

The term "aryl" refers to both unsubstituted or substituted hydrocarbon aryl moieties and heteroaryl moieties. Examples of hydrocarbon aryl moieties include substituted or unsubstituted phenyl, naphthyl, pyrenyl, anthryl, and phenanthryl. Examples of heteroaryl moieties include furyl, pyrrolyl, thienyl, oxazoyl, imidazoyl, thiazoyl, pyridyl, pyrimidinyl, quinazolinyl and indolyl. The substituent of the aryl or benzyl can be chosen, for example, from $C_1$-$C_6$ alkyl, $OR^a$; halo, cyano, nitro, $NH_2$, $NHR^b$, $N(R^b)_2$, a $C_3$-$C_6$ cyclic alkylamino group, or a methylenedioxy or ethylenedioxy group; wherein $R^a$ is hydrogen or $C_1$-$C_{10}$ alkyl, and $R^b$ is hydrogen or $C_1$-$C_{10}$ alkyl. The number of the substituent in not limited and can be from 1 to 5;

Examples of the compounds of Formula I may be selected from:

(1-Methylbenzo[d]pyrrolo[2,1-b]thiazole-2,3-diyl)dimethanol;
(1-(4-Fluorophenyl)benzo[d]pyrrolo[2,1-b]thiazole-2,3-diyl)dimethanol;
(1-(4-Chlorophenyl)benzo[d]pyrrolo[2,1-b]thiazole-2,3-diyl)dimethanol;
(1-(3,4-Difluorophenyl)benzo[d]pyrrolo[2,1-b]thiazole-2,3-diyl)dimethanol;
(1-(3,4-Dichlorophenyl)benzo[d]pyrrolo[2,1-b]thiazole-2,3-diyl)dimethanol;
(1-(3-Chloro-4-fluorophenyl)benzo[d]pyrrolo[2,1-b]thiazole-2,3-diyl)dimethanol;
(1-(4-Methoxyphenyl)benzo[d]pyrrolo[2,1-b]thiazole-2,3-diyl)dimethanol;
(1-(3,4-Dimethoxyphenyl)benzo[d]pyrrolo[2,1-b]thiazole-2,3-diyl)dimethanol;
(1-(3,4,5-Trimethoxyphenyl)benzo[d]pyrrolo[2,1-b]thiazole-2,3-diyl)dimethanol and
(1-Cyclopropylbenzo[d]pyrrolo[2,1-b]thiazole-2,3-diyl)dimethanol.

In another aspect, the present application discloses compounds of Formula II:

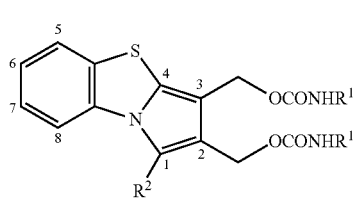

Formula II wherein:

$R^1$ and $R^2$ are the same or different, and are hydrogen, a $C_1$-$C_5$ linear, branched or cyclic alkyl group, an aryl or a benzyl, which may be unsubstituted or substituted;

The term "aryl" refers to both unsubstituted or substituted hydrocarbon aryl moieties and heteroaryl moieties. Examples of hydrocarbon aryl moieties include substituted or unsubstituted phenyl, naphthyl, pyrenyl, anthryl, and phenanthryl. Examples of heteroaryl moieties include furyl, pyrrolyl, thienyl, oxazoyl, imidazoyl, thiazoyl, pyridyl, pyrimidinyl, quinazolinyl and indolyl. The substituent of the aryl or benzyl can be chosen, for example, from $C_1$-$C_6$ alkyl, $OR^a$; halo, cyano, nitro, $NH_2$, $NHR^b$, $N(R^b)_2$, a $C_3$-$C_6$ cyclic alkylamino group, or a methylenedioxy or ethylenedioxy group; wherein $R^a$ is hydrogen or $C_1$-$C_{10}$ alkyl, and $R^b$ is hydrogen or $C_1$-$C_{10}$ alkyl. The number of the substituent in not limited and can be from 1 to 5

Examples of the compounds of Formula II may be selected from:

(1-Methylbenzo[d]pyrrolo[2,1-b]thiazole-2,3-diyl)bis(methylene)bis(ethylcarbamate);
(1-(4-Fluorophenyl)benzo[d]pyrrolo[2,1-b]thiazole-2,3-diyl)bis(methylene)bis(ethylcarbamate);
(1-(4-Chlorophenyl)benzo[d]pyrrolo[2,1-b]thiazole-2,3-diyl)bis(methylene)bis(ethylcarbamate);
(1-(3,4-Difluorophenyl)benzo[d]pyrrolo[2,1-b]thiazole-2,3-diyl)bis(methylene)bis(ethylcarbamate);
(1-(3,4-Dichlorophenyl)benzo[d]pyrrolo[2,1-b]thiazole-2,3-diyl)bis(methylene)bis(ethylcarbamate);
(1-(3-Chloro-4-fluorophenyl)benzo[d]pyrrolo[2,1-b]thiazole-2,3-diyl)bis(methylene)bis(ethylcarbamate);
(1-(4-Methoxyphenyl)benzo[d]pyrrolo[2,1-b]thiazole-2,3-diyl)bis(methylene)bis(ethylcarbamate);
(1-(3,4-Dimethoxyphenyl)benzo[d]pyrrolo[2,1-b]thiazole-2,3-diyl)bis(methylene)bis(ethylcarbamate);
(1-(3,4,5-Trimethoxyphenyl)benzo[d]pyrrolo[2,1-b]thiazole-2,3-diyl)bis(methylene)bis(ethylcarbamate);
(1-Cyclopropylbenzo[d]pyrrolo[2,1-b]thiazole-2,3-diyl)bis(methylene)bis(ethylcarbamate);
(1-Methylbenzo[d]pyrrolo[2,1-b]thiazole-2,3-diyl)bis(methylene)bis(isopropyl-carbamate);
(1-(4-Fluorophenyl)benzo[d]pyrrolo[2,1-b]thiazole-2,3-diyl)bis(methylene)bis(iso-propylcarbamate);
(1-(4-Chlorophenyl)benzo[d]pyrrolo[2,1-b]thiazole-2,3-diyl)bis(methylene)bis(iso-propylcarbamate);
(1-(3,4-Difluorophenyl)benzo[d]pyrrolo[2,1-b]thiazole-2,3-diyl)bis(methylene)bis(iso-propylcarbamate);
(1-(3,4-Dichlorophenyl)benzo[d]pyrrolo[2,1-b]thiazole-2,3-diyl)bis(methylene)bis(iso-propylcarbamate);
(1-(3-Chloro-4-fluorophenyl)benzo[d]pyrrolo[2,1-b]thiazole-2,3-diyl)bis(methylene)bis(iso-propylcarbamate);
(1-(4-Methoxyphenyl)benzo[d]pyrrolo[2,1-b]thiazole-2,3-diyl)bis(methylene)bis(iso-propylcarbamate);
(1-(3,4-Dimethoxyphenyl)benzo[d]pyrrolo[2,1-b]thiazole-2,3-diyl)bis(methylene)bis(iso-propylcarbamate);
(1-(3,4,5-Trimethoxyphenyl)benzo[d]pyrrolo[2,1-b]thiazole-2,3-diyl)bis(methylene)bis(iso-propylcarbamate) and
(1-Cyclopropylbenzo[d]pyrrolo[2,1-b]thiazole-2,3-diyl)bis(methylene)bis(iso-propyl-carbamate).

In another aspect, the present application discloses compounds of Formula III:

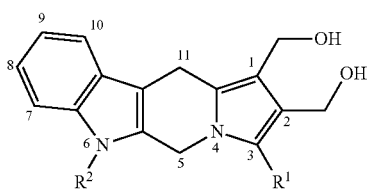

Formula III wherein:

$R^1$ is hydrogen, a $C_1$-$C_5$ linear, branched or cyclic alkyl group, an aryl or a benzyl, which may be unsubstituted or substituted;

The term "aryl" refers to both unsubstituted or substituted hydrocarbon aryl moieties and heteroaryl moieties. Examples of hydrocarbon aryl moieties include substituted or unsubstituted phenyl, naphthyl, pyrenyl, anthryl, and phenanthryl. Examples of heteroaryl moieties include furyl, pyrrolyl, thienyl, oxazoyl, imidazoyl, thiazoyl, pyridyl, pyrimidinyl, quinazolinyl and indolyl. The substituent of the aryl or benzyl can be chosen, for example, from $C_1$-$C_6$ alkyl, $OR^a$; halo, cyano, nitro, $NH_2$, $NHR^b$, $N(R^b)_2$, a $C_3$-$C_6$ cyclic alkylamino group, or a methylenedioxy or ethylenedioxy group; wherein $R^a$ is hydrogen or $C_1$-$C_{10}$ alkyl, and $R^b$ is hydrogen or $C_1$-$C_{10}$ alkyl. The number of the substituent in not limited and can be from 1 to 5;

$R^2$ is hydrogen, a $C_1$-$C_5$ linear, branched or cyclic alkyl group, a benzyl, which may be unsubstituted or substituted, an acyl ($R^aCO$), a methansulfonyl ($Me_2SO_2$), or a toluenesulfonyl $MeC_6H_4SO_2$); wherein $R^a$ is a $C_1$-$C_5$ linear, branched or cyclic alkyl group, an aryl or a benzyl, which may be unsubstituted or substituted;

Examples of the compounds of Formula III may be selected from:

(3-(phenyl)-6-methyl-6,11-dihydro-5H-indolizino[6,7-b]indole-1,2-diyl)dimethanol;

(3-(4-Fluorophenyl)-6-methyl-6,11-dihydro-5H-indolizino [6,7-b]indole-1,2-diyl)dimethanol;

3-(4-Chlorophenyl)-6-methyl-6,11-dihydro-5H-indolizino [6,7-b]indole-1,2-diyl)dimethanol;

(3-(3,4-Difluorophenyl)-6-methyl-6,11-dihydro-5H-indolizino[6,7-b]indole-1,2-diyl)dimethanol;

[6-Methyl-3-phenyl-6,11-dihydro-5H-indolizino[6,7-b]indole-1,2-diyl]bis(methylene)bis(ethylcarbamate);

[3-(4-Fluorophenyl)-6-methyl-6,11-dihydro-5H-indolizino [6,7-b]indole-1,2-diyl]bis(methylene)bis(ethylcarbamate);

[3-(4-Chlorophenyl)-6-methyl-6,11-dihydro-5H-indolizino [6,7-b]indole-1,2-diyl]bis(methylene)bis(ethylcarbamate) and

[3-(4-Difluorophenyl)-6-methyl-6,11-dihydro-5H-indolizino[6,7-b]indole-1,2-diyl]bis(methylen)bis(ethylcarbamate).

In another aspect, the present application discloses compounds of Formula IV:

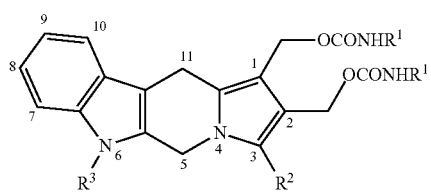

Formula IV wherein:

$R^1$ and $R^2$ are the same or different, and are hydrogen, a $C_1$-$C_5$ linear, branched or cyclic alkyl group, an aryl or a benzyl, which may be unsubstituted or substituted;

The term "aryl" refers to both unsubstituted or substituted hydrocarbon aryl moieties and heteroaryl moieties. Examples of hydrocarbon aryl moieties include substituted or unsubstituted phenyl, naphthyl, pyrenyl, anthryl, and phenanthryl. Examples of heteroaryl moieties include furyl, pyrrolyl, thienyl, oxazoyl, imidazoyl, thiazoyl, pyridyl, pyrimidinyl, quinazolinyl and indolyl. The substituent of the aryl or benzyl can be chosen, for example, from $C_1$-$C_6$ alkyl, $OR^a$; halo, cyano, nitro, $NH_2$, $NHR^b$, $N(R^b)_2$, a $C_3$-$C_6$ cyclic alkylamino group, or a methylenedioxy or ethylenedioxy group; wherein $R^a$ is hydrogen or $C_1$-$C_{10}$ alkyl, and $R^b$ is hydrogen or $C_1$-$C_{10}$ alkyl. The number of the substituent in not limited and can be from 1 to 5

$R^3$ is hydrogen, a $C_1$-$C_5$ linear, branched or cyclic alkyl group, a benzyl, which may be unsubstituted or substituted, an acyl ($R^aCO$), a methansulfonyl ($Me_2SO_2$), or a toluenesulfonyl $MeC_6H_4SO_2$); wherein $R^a$ is a $C_1$-$C_5$ linear, branched or cyclic alkyl group, an aryl or a benzyl, which may be unsubstituted or substituted;

Examples of the compounds of Formula IV may be selected from:

[6-Methyl-3-phenyl-6,11-dihydro-5H-indolizino[6,7-b]indole-1,2-diyl]bis(methylene)bis(iso propylcarbamate);

[3-(4-Fluorophenyl)-6-methyl-6,11-dihydro-5H-indolizino [6,7-b]indole-1,2-diyl]bis(methylene) (isopropylcarbamate);

[3-(4-Chlorophenyl)-6-methyl-6,11-dihydro-5H-indolizino [6,7-b]indole-1,2-diyl]bis(methylene) (isopropylcarbamate) and

[3-(3,4-Difluorophenyl)-6-methyl-6,11-dihydro-5H-indolizino[6,7-b]indole-1,2-diyl]bis(methylene) (isopropylcarbamate).

The synthesis method of the above compounds of Formulae I-IV includes starting with a compound of Formula V, VI, VII, VIII, IX, or X:

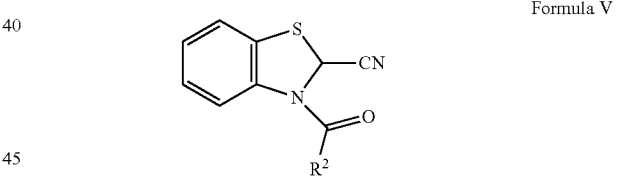

Formula V

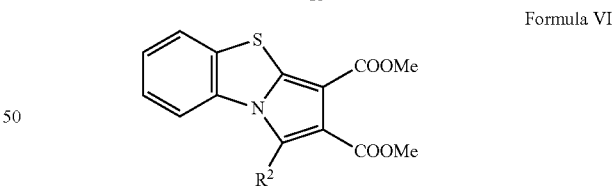

Formula VI

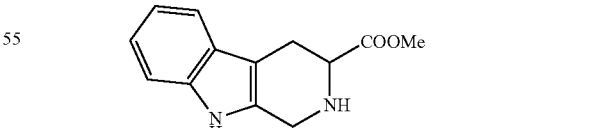

Formula VII

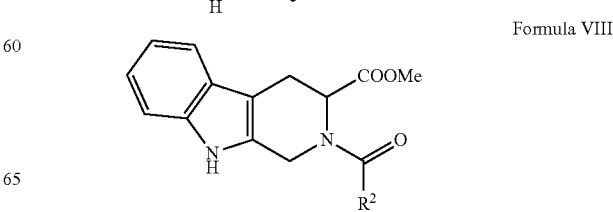

Formula VIII

-continued

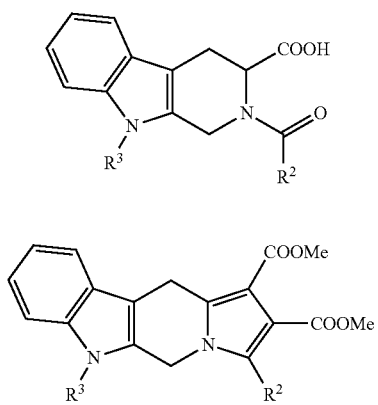

Formula IX

Formula X

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PRESENTLY PREFERRED EMBODIMENTS

Figure 1:
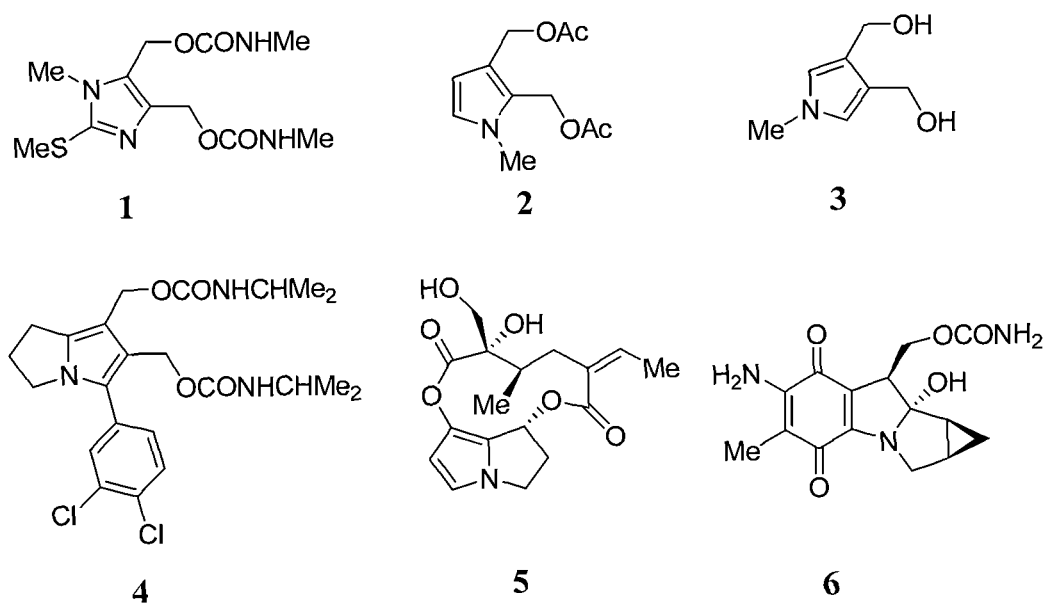
FIG. 1 shows various DNA bifunctional alkylating agents developed originally from the pyrrolizine alkaloid (5).
Figure 2:
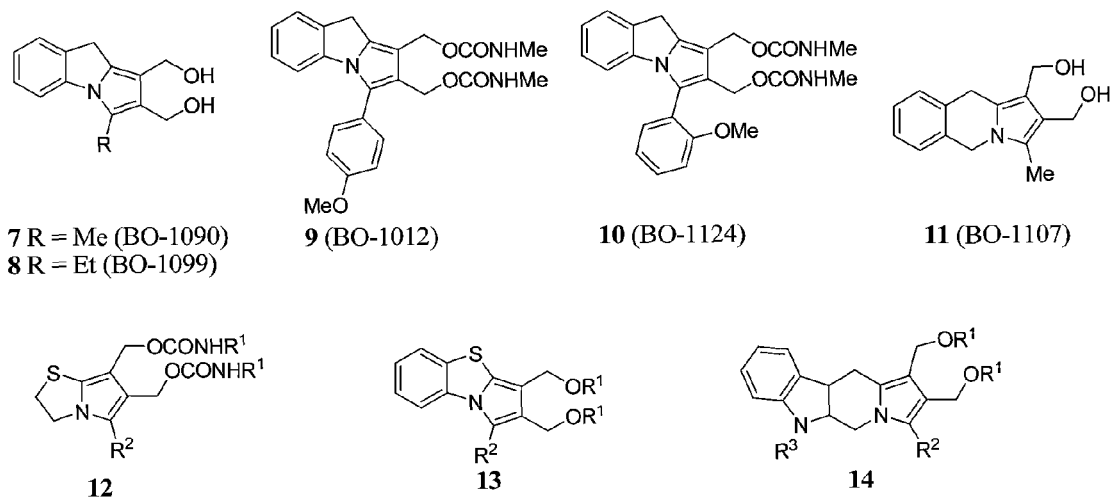
FIG. 2 shows the chemical structures of various compounds including bis(carbamoylmethyl) derivatives of pyrrolo[2,1-a] isoquinoline, bis(hydroxymethyl) derivatives, dihydropyrrolo[2,1-b]thiazole, and 1,2-bis(hydroxymethyl) indolizino[6,7-b]indole derivatives.
Figure 3:
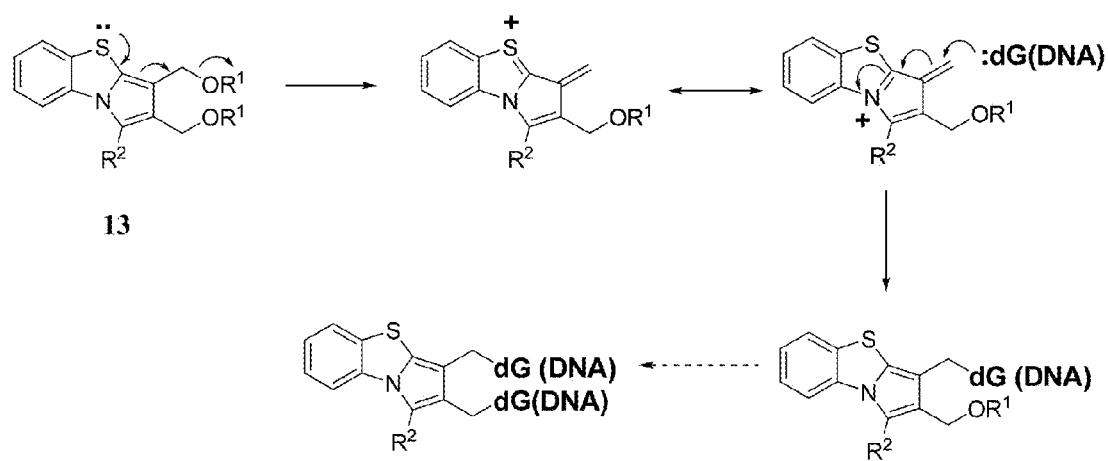
FIG. 3 shows a proposed mechanism of action of DNA cross-linking by 2,3-bis(hydroxymethyl)-4H-benzo[d]pyrrolo[1,2-c]thiazoles and their bis(alkylcarbamates).

The compounds disclosed herein can be synthesized using conventional techniques. For example, these compounds can conveniently be synthesized from readily available starting materials using standard organic chemistry synthesis methods, including those methods illustrated in the schemes and the examples herein.

General Procedure

An exemplary scheme of synthesizing 2,3-bis-(hydroxymethyl)-4H-benzo[d]pyrrolo[1,2-a]thiazoles (Formula I) and their bis(carbamate) derivatives (Formula II) is presented in Scheme 2, wherein $R^1$, $R^2$, $R^3$, $R^4$, $R^5$, and $R^6$ are defined above. An exemplary scheme of synthesis of (1-hydroxymethyl-5,10-dihydro-pyrrolo[1,2-b]isoquinolin-2-yl)methanol (Formula III) and their bis(carbamate) derivatives (Formula IV) is shown in Scheme 3.

Compounds of Formulae I and II can be synthesized as shown in Scheme 2. Compound 16 can be synthesized from the commercially available benzothiazole 15 according to the literature procedure.[16] By following the method described previously,[17] compounds 16 can be converted into diester 17 by treating with tetrafluoro boric acid in ether followed with N,N-dimethyl acetylenedicarboxylate (DMAD). The diester functions of 17 can be reduced to the corresponding bis-alcohol derivatives 18 (Formula I) by reacting with LiAlH$_4$ in a mixture of ether/CH$_2$Cl$_2$ in an ice bath. Treatment of 18 with various alkyl, phenyl, or benzylisocyantes in the presence of base (e.g. triethylamine or pyridine) can afford the desired bis(alkylcarbamate) derivatives 19, and 20 (Formula II).

Scheme 2

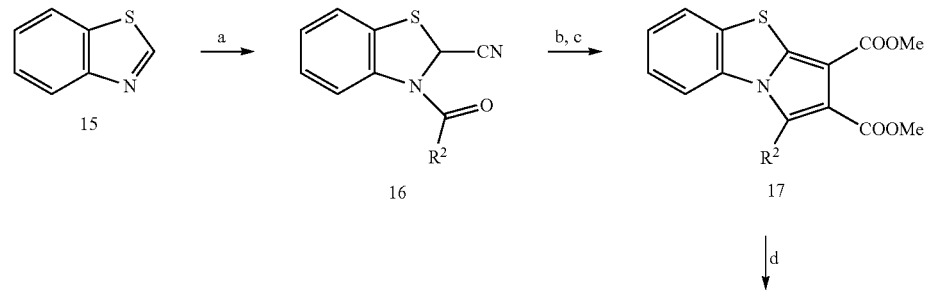

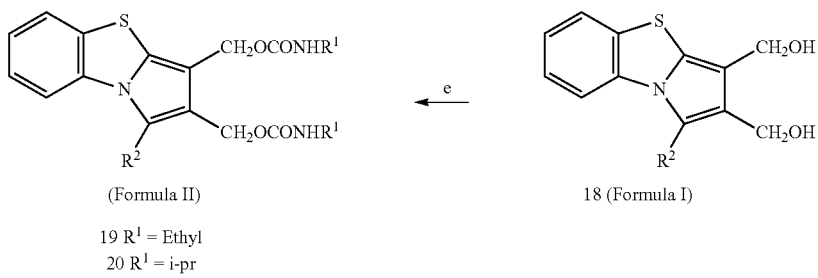

19 R¹ = Ethyl
20 R¹ = i-pr

Reaction conditions: a) Acid chloride (R²COCl)/AlCl₃, trimethylsilyl cyanide/CH₂Cl₂, room temperature; b) tetrafluoroboric acid in ether; c) DMAD/DMF, ambient temperature; d) LiAlH₄/CH₂Cl₂/Et₂O, 0° C.; e) R¹NCO/Et₃N Compounds of Formulae III and IV can be synthesized as shown in Schemes 3. Reaction of tryptophane methylester hydrochloride (21) with formaldehyde can yield 22 by Pictet Spengler cyclization.[18,19] N-Acylation of 22 with various acid chloride or acid anhydrides in presence of base (such as triethylamine or pyridine) in an appropriate solvent (such as CHCl₃, THF, or DMF) can give compound 23, which can be then reacted with a variety of alkyl or substituted benzyl halides (such as methyl iodide, ethyl iodide, or benzyl bromide) to give product 24. Treatment of 24 with DMAD in acetic anhydride 60-75° C. can afford di-esters 25 by the known procedure as described previously.[20] Reduction of 25 with LiAlH₄ in ether/CH₂Cl₂ can afford the desired bis(hydroxymethyl) derivatives 26 (Formula III). Similarly, reaction of 26 with various alkyl, phenyl, or benzylisocyantes in the presence of base (e.g. triethylamine or pyridine) can afford the desired bis(alkylcarbamate) derivatives 27 (Formula IV).

Scheme 3

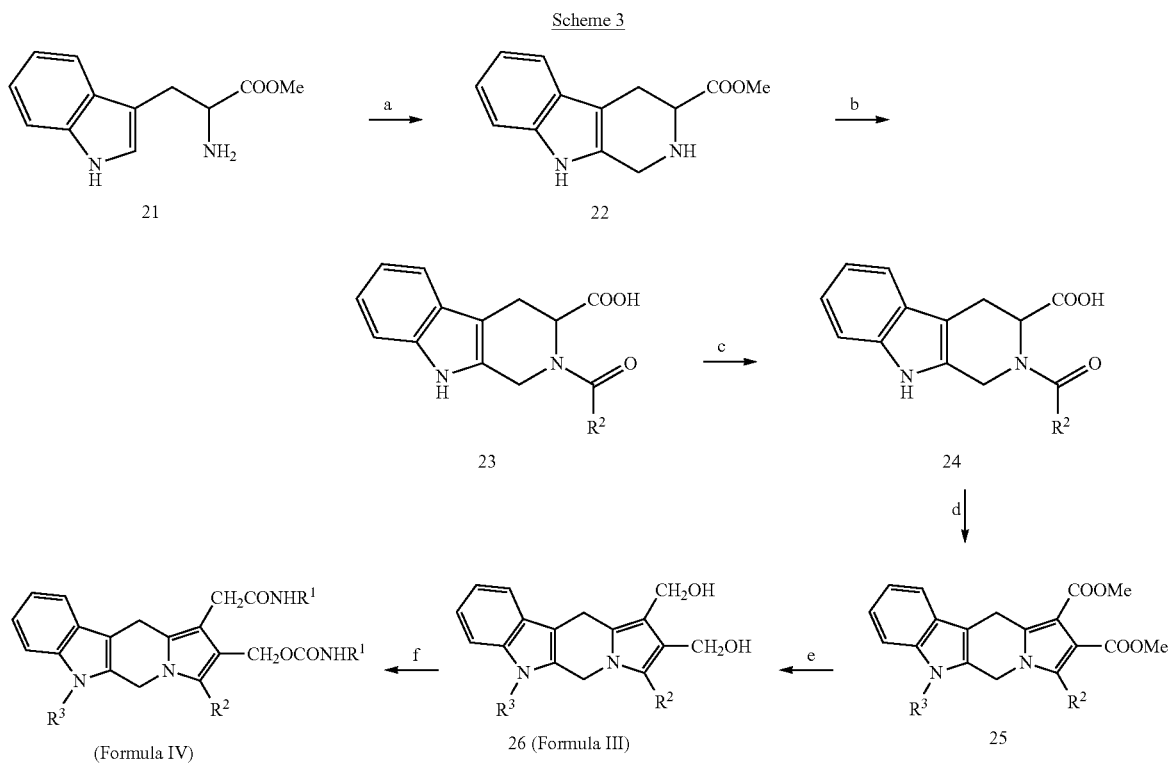

27 R¹ = Et
28 R¹ = i-pr

Reaction conditions: a) formaldehyde/MeOH; b) R²COCl/Et₃N; c) alkyl halides, benzyl halides, methanesulfonyl chloride or toluenesulfonyl chloride/NaH/THF; d) DMAD/Ac₂O, 60-70° C.; e) LiAlH₄/CH₂Cl₂/Et₂O; f) R¹NCO/Et₃N.

Alternatively, compounds having a Me function at C3 of indolizino[6,7-b]indole derivatives can be prepared as shown in Scheme 4. The commercially available L-tryptophane (29) can be converted into compound 30 by the method as described previously. Treatment of 30 with DMAD in acetic anhydride upon heating can give diester 31, which can be then reacted with various alkyl halides (such as MeI, EtI) or benzyl halides (such as benzyl bromide) to yield 32. Similarly, compounds 32 can be converted into the desired bis(hydroxymethyl) (Formula III) and bis(alkylcarbamate) derivatives (Formula IV) as described previously.

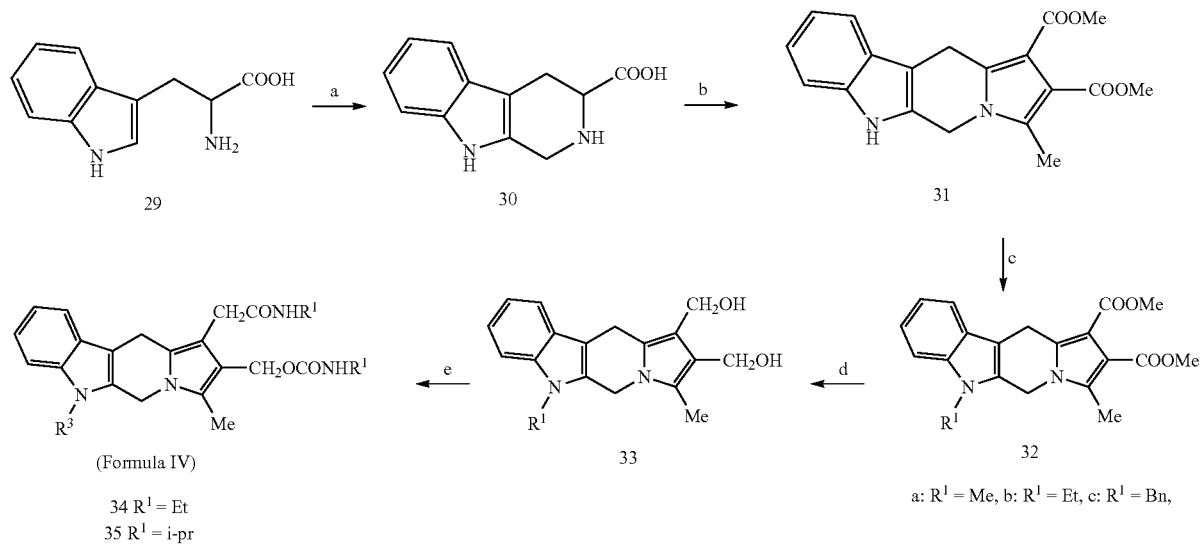

Scheme 4 a: R¹ = Me, b: R¹ = Et, c: R¹ = Bn;

Reaction conditions: (a) formaldehyde/sulfuric acid; (b) DMAD/AC₂O, 70° C.; (c) NaH/DMF/R¹—I or R¹—Br; (d) LiAlH₄/ether/CH₂Cl₂, 0° C.; (e) R²NCO/TEA.

The specific examples below are merely illustrative, and not limitative to the present disclosure.

2,3-Bis(hydroxymethyl)-4H-benzo[d]pyrrolo-[1,2-a]thiazoles Formula I) and their bis(alkylcarbamates) derivatives (Formula II)

Example 1

Synthesis of (1-methylbenzo[d]pyrrolo[2,1-b]thiazole-2,3-diyl)dimethanol (BO-1595), (1-methylbenzo[d]pyrrolo[2,1-b]thiazole-2,3-diyl)-bis(methylene)bis(ethylcarbamate) (BO-1653) and (1-methylbenzo[d]pyrrolo[2,1-b]thiazole-2,3-diyl)bis(methylene)bis(isopropylcarbamate) (BO-1652)

1) 3-Acetyl-2,3-dihydrobenzo[d]thiazole-2-carbonitrile

Acetylchloride (4.00 g, 51.0 mmol) was added dropwise to a stirring solution of benzothiazole (6.75 g, 50.0 mmol) in dichloromethane (40 mL) under argon atmosphere. A catalytic amount of $AlCl_3$ and trimethylsilylcyanide (5.1 g, 52.0 mmol) were than added into the reaction mixture. After being stirred for 17 h at room temperature, the reaction mixture was evaporated to dryness in vacuo and the residue was triturated with ether to give 3-acetyl-2,3-dihydrobenzo[d]thiazole-2-carbonitrile, 8.2 g (80%); mp 92-93° C. $^1$H NMR (DMSO-$d_6$) δ 2.39 (3H, s, Me), 7.05 (1H, s, ArH), 7.16-7.26 (2H, m, 2×ArH), 7.49-7.51 (1H, m, ArH), 7.65 (1H, brs, C2-H). Anal. Calcd. for ($C_{10}H_8N_2OS$): C, 58.80; H, 3.95; N, 13.72; S, 15.70. Found: C, 58.85; H, 3.95; N, 13.78; S, 15.76.

2) Dimethyl 1-methylbenzo[d]pyrrolo[2,1-b]thiazole-2,3-dicarboxylate

To a solution of 3-acetyl-2,3-dihydrobenzo[d]thiazole-2-carbonitrile (5 g, 24.5 mmol) in dichloromethane (50 mL) was added dropwise 7 mL of tetrafluoroboric acid ($HBF_4$). The solution was stirred for 3 h at room temperature. The brown precipitates appeared were collected by filtration and the filter cake was washed with ether. The solid salt was added to a solution of dimethyl acetylenedicarboxylate (10.4 g, 73.0 mmol) in DMF (30 mL) and then warmed at 35° C. for 13 h. The reaction mixture was concentrated in vacuo and the residue was recrystallized from methanol to give dimethyl 1-methylbenzo[d]pyrrolo[2,1-b]thiazole-2,3-dicarboxylate, 1.7 g (23%); mp 143-144° C. $^1$H NMR (DMSO-$d_6$) δ 2.85 (3H, s, Me), 3.83 (3H, s, COOMe), 3.85 (3H, s, COOMe), 7.50 (1H, t, J=7.6 Hz, ArH), 7.58 (1H, t, J=7.6 Hz, ArH), 8.07 (1H, d, J=8.0 Hz, ArH), 8.12 (1H, d, J=8.0 Hz, ArH). Anal. Calcd. for ($C_{15}H_{13}NO_4S$): C, 59.39; H, 4.32; N, 4.62; S, 10.57. Found: C, 59.02; H, 4.23; N, 4.87; S, 10.42.

3) (1-Methylbenzo[d]pyrrolo[2,1-b]thiazole-2,3-diyl)dimethanol (BO-1595)

A solution of dimethyl 1-methylbenzo[d]pyrrolo[2,1-b]thiazole-2,3-dicarboxylate (2.0 g, 6.6 mmol) in anhydrous dichloromethane (30 mL) was added dropwise to a stirred mixture of lithium aluminum hydride (0.6 g, 16.0 mmol) in anhydrous ether (20 mL) at −5° C. to 0° C. The reaction mixture was allowed to stir at this temperature for 20 min. The excess hydride was decomposed by adding water (1 mL) followed by $NH_4OH$ (1 mL) and water (1 mL) at −5° C. to 0° C. The mixture was filtered through a pad of Celite, washed with several times with dichloromethane. The combined filtrate and washings were washed successively with water and brine solution. The organic layer was dried ($Na_2SO_4$) and concentrated to dryness in vacuum. The residue was triturated with ether to give (1-methylbenzo[d]pyrrolo[2,1-b]thiazole-2,3-diyl) dimethanol (BO-1595), 1.3 g (82%) as white powder; mp 138-139° C. $^1$H NMR (DMSO-$d_6$) δ 2.63 (3H, s, Me), 4.39 (2H, d, J=5.2 Hz, $CH_2$), 4.56 (2H, d, J=5.2 Hz, $CH_2$), 4.60 (1H, t, J=5.6 Hz, exchangeable, OH), 4.97 (1H, t, J=5.6 Hz, exchangeable, OH), 7.21-7.25 (1H, m, ArH), 7.34-7.38 (1H, m, ArH), 7.76-7.78 (1H, m, ArH), 7.83-7.85 (1H, m, ArH). Anal. Calcd. for ($C_{13}H_{13}NO_2S$): C, 63.13; H, 5.30; N, 5.66; S, 12.97. Found: C, 62.94; H, 5.24; N, 5.83; S, 12.90.

4) (1-Methylbenzo[d]pyrrolo[2,1-b]thiazole-2,3-diyl)bis(methylene)bis(ethylcarbamate) (BO-1653)

A solution of (1-methylbenzo[d]pyrrolo[2,1-b]thiazole-2,3-diyl)dimethanol (BO-1595) (0.24 g, 1.0 mmol) in anhydrous THF was treated with excess triethylamine (0.5 mL) followed by excess ethylisocyanate (0.28 g, 4.0 mmol). The reaction mixture was stirred at ambient temperature under an argon atmosphere. After the completion of the reaction, the reaction mixture was evaporated to dryness in vacuo. The residue was recrystallized from ethanol to give BO-1653, 0.30 g (85%); mp 158-159° C. $^1$H NMR (DMSO-$d_6$) δ 0.98 (6H, t, J=7.0 Hz, 2×Me), 2.67 (3H, s, Me), 2.98 (4H, q, J=7.0 Hz, $CH_2$), 5.01 (2H, s, $CH_2$), 5.03 (2H, s, $CH_2$), 7.02-7.05 (2H, brs, exchangeable, NH), 7.29 (1H, t, J=8.0 Hz, ArH), 7.41 (1H, t, J=8.0 Hz, ArH), 7.84 (1H, d, J=8.0 Hz, ArH), 7.91 (1H, d, J=8.0 Hz, ArH). Anal. Calcd. for ($C_{19}H_{23}N_3O_4S$): C, 58.59; H, 5.95; N, 10.79; S, 8.23. Found: C, 58.26; H, 5.62; N, 10.46; S, 8.60.

5) (1-Methylbenzo[d]pyrrolo[2,1-b]thiazole-2,3-diyl)bis(methylene)bis(isopropyl-carbamate) (BO-1652)

A solution of (1-methylbenzo[d]pyrrolo[2,1-b]thiazole-2,3-diyl)dimethanol (BO-1595) (0.24 g, 1.0 mmol) in anhydrous THF was treated with excess triethylamine (0.5 mL) followed by excess isopropylisocyanate (0.34 g, 4.0 mmol). The reaction mixture was stirred at ambient temperature under an argon atmosphere. After being stirred overnight, the reaction mixture was evaporated to dryness in vacuo. The residue was recrystallized from ethanol to give (1-methylbenzo[d]pyrrolo[2,1-b]thiazole-2,3-diyl)bis(methylene)bis(isopropyl-carbamate) (BO-1652), 0.33 g (79%); mp 172-173° C. $^1$H NMR (DMSO-$d_6$) δ 1.03 (12H, d, J=6.4 Hz, 4×Me), 2.67 (3H, s, Me), 3.59 (2H, m, CH), 5.02 (2H, s, $CH_2$), 5.04 (2H, s, $CH_2$), 6.97-6.99 (2H, brs, exchangeable, NH), 7.29 (1H, t, J=8.0 Hz, ArH), 7.41 (1H, t, J=8.0 Hz, ArH), 7.84 (1H, d, J=8.0 Hz, ArH), 7.91 (1H, d, J=8.0 Hz, ArH). Anal. Calcd. for ($C_{21}H_{27}N_3O_4S$): C, 60.41; H, 6.52; N, 10.06; S, 7.68. Found: C, 60.08; H, 6.24; N, 9.76; S, 7.97.

Example 2

Synthesis of (1-(4-fluorophenyl)benzo[d]pyrrolo[2,1-b]thiazole-2,3-diyl)dimethanol (BO-1592), (1-(4-fluorophenyl)benzo[d]pyrrolo[2,1-b]thiazole-2,3-diyl)bis(methylene)bis(ethylcarbamate) (BO-1593) and (1-(4-fluorophenyl)benzo[d]pyrrolo[2,1-b]thiazole-2,3-diyl)bis(methylene)bis(iso-propylcarbamate) (BO-1597)

1) 3-(4-Fluorobenzoyl)-2,3-dihydrobenzo[d]thiazole-2-carbonitrile

4-Fluorobenzoylchloride (6.5 g, 41.0 mmol) was added dropwise to a stirring solution of benzothiazole (5.4 g, 40.0 mmol) in dichloromethane (40 mL) under argon atmosphere. A catalytic amount of $AlCl_3$ and trimethylsilylcyanide (4.1 g, 42.0 mmol) were than added into the reaction mixture. After being stirred for 15 h at room temperature, the reaction mixture was evaporated to dryness in vacuo and the residue was triturated with ether to give 3-(4-fluorobenzoyl)-2,3-dihydrobenzo[d]thiazole-2-carbonitrile, 9.3 g (82%); mp 150-151° C. $^1$H NMR (DMSO-$d_6$) δ 6.71 (1H, brs, C2-H), 6.85 (1H, s, ArH), 7.04-7.07 (1H, m, ArH), 7.12-7.16 (1H, m, ArH), 7.38-7.40 (2H, m, 2×ArH), 7.52-7.54 (1H, m, ArH), 7.64-7.67 (2H, m, 2×ArH). Anal. Calcd. for ($C_{15}H_9FN_2OS$): C, 63.37; H, 3.19; N, 9.85; S, 11.28. Found: C, 63.02; H, 3.27; N, 9.81; S, 11.31.

2) Dimethyl 1-(4-fluorophenyl)benzo[d]pyrrolo[2,1-b]thiazole-2,3-dicarboxylate To a solution of 3-(4-fluorobenzoyl)-2,3-dihydrobenzo[d]thiazole-2-carbonitrile (8.1 g, 28.0 mmol) in dichloromethane (50 mL) was added dropwise 8 mL of tetrafluoroboric acid ($HBF_4$). The solution was stirred for 3 h at room temperature. The brown precipitates appeared were collected by filtration and the filter cake was washed with ether. The solid salt was added to a solution of dimethyl acetylenedicarboxylate (12.2 g, 84.0 mmol) in DMF (40 mL) and then warmed at 35° C. for 14 h. The reaction mixture was concentrated in vacuo and the residue was crystallized from methanol to give dimethyl 1-(4-fluorophenyl)benzo[d]pyrrolo[2,1-b]thiazole-2,3-dicarboxylate, 2.5 g (23%); mp 186-187° C. $^1$H NMR (DMSO-$d_6$) δ 3.63 (3H, s, COOMe), 3.83 (3H, s, COOMe), 6.78-6.80 (1H, m, ArH), 7.28-7.30 (1H, m, ArH), 7.30-7.44 (3H, m, 3×ArH), 7.62-7.66 (2H, m, 2×ArH), 8.03-8.05 (1H, m, ArH). Anal. Calcd. for ($C_{20}H_{14}FNO_4S$): C, 62.65; H, 3.68; N, 3.65; S, 8.36. Found: C, 62.68; H, 3.46; N, 3.62; S, 8.76.

3) (1-(4-Fluorophenyl)benzo[d]pyrrolo[2,1-b]thiazole-2,3-diyl)dimethanol (BO-1592)

A solution of dimethyl 1-(4-fluorophenyl)benzo[d]pyrrolo[2,1-b]thiazole-2,3-dicarboxylate (2.4 g, 6.6 mmol) in anhydrous dichloromethane (30 mL) was added dropwise to a stirred mixture of lithium aluminum hydride (0.6 g, 16.0 mmol) in anhydrous ether (20 mL) at −5° C. to 0° C. The reaction mixture was allowed to stir at this temperature for 20 min. The excess hydride was decomposed by adding water (1 mL) followed by $NH_4OH$ (1 mL) and water (1 mL) at −5° C. to 0° C. The mixture was filtered through a pad of Celite, washed with several times with dichloromethane. The combined filtrate and washings were washed successively with water and brine solution. The organic layer was dried ($Na_2SO_4$) and concentrated to dryness in vacuo. The residue was triturated with ether to give (1-(4-fluorophenyl)benzo[d]pyrrolo[2,1-b]thiazole-2,3-diyl)dimethanol (BO-1592), 1.5 g (76%); mp 155-156° C. $^1$H NMR (DMSO-$d_6$) δ 4.22 (2H, d, J=5.1 Hz, $CH_2$), 4.66 (2H, d, J=5.1 Hz, $CH_2$), 4.73 (1H, t, J=5.1 Hz, exchangeable, OH), 5.13 (1H, t, J=5.1 Hz, exchangeable, OH), 6.83-6.85 (1H, m, ArH), 7.15-7.19 (2H, m, 2×ArH), 7.37-7.41 (2H, m, 2×ArH), 7.53-7.57 (2H, m, 2×ArH), 7.79-7.81 (1H, m, ArH). Anal. Calcd. for ($C_{18}H_{14}FNO_2S$): C, 66.04; H, 4.31; N, 4.28; S, 9.79. Found: C, 65.25; H, 4.22; N, 4.14; S, 9.76.

4) (1-(4-Fluorophenyl)benzo[c]pyrrolo[2,1-b]thiazole-2,3-diyl)bis(methylene)bis(ethylcarbamate) (BO-1593)

A solution of (1-(4-fluorophenyl)benzo[d]pyrrolo[2,1-b]thiazole-2,3-diyl)dimethanol (BO-1592) (0.33 g, 1.0 mmol)

in anhydrous THF was treated with excess triethylamine (0.5 mL) followed by excess ethylisocyanate (0.28 g, 4.0 mmol). The reaction mixture was stirred at ambient temperature under an argon atmosphere. After being stirred overnight, the reaction mixture was evaporated to dryness in vacuo. The residue was recrystallized from ethanol to give 1-(4-fluorophenyl)benzo[d]pyrrolo[2,1-b]thiazole-2,3-diyl)bis(methylene)bis(ethylcarbamate) (BO-1593), 0.36 g (79%); mp 172-173° C. $^1$H NMR (DMSO-$d_6$) δ 0.98 (6H, t, J=7.0 Hz, 2×Me), 2.98 (4H, q, J=7.0 Hz, $CH_2$), 4.81 (2H, s, $CH_2$), 5.12 (2H, s, $CH_2$), 6.79-6.81 (1H, m, ArH), 7.05-7.11 (2H, brs, exchangeable, NH), 7.19-7.26 (2H, m, 2×ArH), 7.38-7.43 (2H, m, 2×ArH), 7.56-7.59 (2H, m, 2×ArH), 7.86-7.88 (1H, m, ArH). Anal. Calcd. for ($C_{24}H_{24}FN_3O_4S$): C, 61.39; H, 5.15; N, 8.95; S, 6.83. Found: C, 61.36; H, 5.26; N, 8.94; S, 7.14.

5) (1-(4-Fluorophenyl)benzo[d]pyrrolo[2,1-b]thiazole-2,3-diyl)bis(methylene)bis(iso-propyl-carbamate) (BO-1597)

A solution of (1-(4-fluorophenyl)benzo[d]pyrrolo[2,1-b]thiazole-2,3-diyl)dimethanol (BO-1592) (0.33 g, 1.0 mmol) in anhydrous THF was treated with excess triethylamine (0.5 mL) followed by excess isopropylisocyanate (0.34 g, 4.0 mmol). The reaction mixture was stirred at ambient temperature under an argon atmosphere. After being stirred overnight, the reaction mixture was evaporated to dryness in vacuo. The residue was recrystallized from ethanol to give (1-(4-fluorophenyl)benzo[d]pyrrolo[2,1-b]thiazole-2,3-diyl)bis(methylene)bis(iso-propyl-carbamate) (BO-1597), 0.47 g (95%); mp 174-175° C. $^1$H NMR (DMSO-$d_6$) δ1.04 (12H, d, J=6.6 Hz, 4×Me), 3.59 (2H, m, CH), 4.81 (2H, s, $CH_2$), 5.12 (2H, s, $CH_2$), 6.79-6.81 (1H, m, ArH), 6.99-7.05 (2H, brs, exchangeable, NH), 7.18-7.26 (2H, m, 2×ArH), 7.38-7.42 (2H, m, 2×ArH), 7.55-7.58 (2H, m, 2×ArH), 7.86-7.88 (1H, m, ArH). Anal. Calcd. for ($C_{26}H_{28}FN_3O_4S$): C, 62.76; H, 5.67; N, 8.44; S, 6.44. Found: C, 62.46; H, 5.61; N, 8.30; S, 6.48.

Example 3

Synthesis (1-(4-chlorophenyl)benzo[d]pyrrolo[2,1-b]thiazole-2,3-diyl)dimethanol (BO-1582), (1-(4-chlorophenyl)benzo[d]pyrrolo[2,1-b]thiazole-2,3-diyl)bis(methylene)bis(ethylcarbamate) (BO-1596), and (1-(4-chlorophenyl)benzo[d]pyrrolo[2,1-b]thiazole-2,3-diyl)bis(methylene)bis(iso-propylcarbamate) (BO-1600)

1) 3-(4-Chlorobenzoyl)-2,3-dihydrobenzo[d]thiazole-2-carbonitrile

4-Chlorobenzoylchloride (7.2 g, 41.0 mmol was added dropwise to a stirring solution of benzothiazole (5.4 g, 40.0 mmol) in dichloromethane (40 mL) under argon atmosphere. A catalytic amount of $AlCl_3$ and trimethylsilylcyanide (4.1 g, 42.0 mmol) were than added into the reaction mixture. After being stirred for 15 h at room temperature, the reaction mixture was evaporated to dryness in vacuo and the residue was triturated with ether to give 3-(4-chlorobenzoyl)-2,3-dihydrobenzo[d]thiazole-2-carbonitrile, 10.1 g (84%); mp 115-117° C. (lit.[21] mp 115-118° C.). $^1$H NMR (DMSO-$d_6$) δ 6.75 (1H, brs, C2-H), 6.85 (1H, s, ArH), 7.05-7.09 (1H, m, ArH), 7.13-7.17 (1H, m, ArH), 7.52-7.54 (1H, m, ArH), 7.58-7.61 (4H, m, 4×ArH).

2) Dimethyl 1-(4-chlorophenyl)benzo[d]pyrrolo[2,1-b]thiazole-2,3-dicarboxylate

To a solution of 3-(4-chlorobenzoyl)-2,3-dihydrobenzo[d]thiazole-2-carbonitrile (9.12 g, 30.0 mmol) in dichloromethane (50 mL) was added dropwise 9 mL of tetrafluoroboric acid ($HBF_4$). The solution was stirred for 3 h at room temperature. The brown precipitates appeared were collected by filtration and the filter cake was washed with ether. The solid salt was added to a solution of dimethyl acetylenedicarboxylate (12.7 g, 90.0 mmol) in DMF (40 mL) and then warmed at 35° C. for 14 h. The reaction mixture was concentrated in vacuo and the residue was crystallized from methanol to give dimethyl 1-(4-chlorophenyl)benzo[d]pyrrolo[2,1-b]thiazole-2,3-dicarboxylate, 2.5 g (21%); mp 172-173° C. $^1$H NMR (DMSO-$d_6$) δ 3.64 (3H, s, COOMe), 3.83 (3H, s, COOMe), 6.85-6.87 (1H, m, ArH), 7.30-7.42 (2H, m, ArH), 7.60-7.66 (4H, m, 4×ArH), 8.04-8.06 (1H, m, ArH). Anal. Calcd. for ($C_{20}H_{14}ClNO_4S.0.5H_2O$): C, 58.75; H, 3.70; N, 3.43; S, 7.84. Found: C, 58.76; H, 3.45; N, 3.59; S, 7.73.

3) (1-(4-Chlorophenyl)benzo[d]pyrrolo[2,1-b]thiazole-2,3-diyl)dimethanol (BO-1582)

A solution of dimethyl 1-(4-chlorophenyl)benzo[d]pyrrolo[2,1-b]thiazole-2,3-dicarboxylate (2.1 g, 5.0 mmol) in anhydrous dichloromethane (30 mL) was added dropwise to a stirred mixture of lithium aluminum hydride (0.45 g, 12.5 mmol) in anhydrous ether (20 mL) at −5° C. to 0° C. The reaction mixture was allowed to stir at this temperature for 20 min. The excess hydride was decomposed by adding water (1 mL) followed by $NH_4OH$ (1 mL) and water (1 mL) at −5° C. to 0° C. The mixture was filtered through a pad of Celite, washed with several times with dichloromethane. The combined filtrate and washings were washed successively with water and brine solution. The organic layer was dried ($Na_2SO_4$) and concentrated to dryness in vacuo. The residue was triturated with ether to give (1-(4-chlorophenyl)benzo[d]pyrrolo[2,1-b]thiazole-2,3-diyl)dimethanol (BO-1582), 1.5 g (88%); mp 151-152° C. $^1$H NMR (DMSO-$d_6$) δ 4.22 (2H, d, J=4.4 Hz, $CH_2$), 4.66 (2H, d, J=4.4 Hz, $CH_2$), 4.76 (1H, t, J=5.2 Hz, exchangeable, OH), 5.14 (1H, t, J=5.2 Hz, exchangeable, OH), 6.91-6.93 (1H, m, ArH), 7.16-7.22 (2H, m, 2×ArH), 7.53 (2H, d, J=8.4 Hz, 2×ArH), 7.61 (2H, d, J=8.4 Hz, 2×ArH), 7.79-7.82 (1H, m, ArH). Anal. Calcd. for ($C_{18}H_{14}ClNO_2S$): C, 62.88; H, 4.10; N, 4.07; S, 9.33. Found: C, 62.73; H, 4.09; N, 4.06; S, 9.19.

4) (1-(4-Chlorophenyl)benzo[d]pyrrolo[2,1-b]thiazole-2,3-diyl)bis(methylene)bis(ethylcarbamate) (BO-1596)

A solution of (1-(4-chlorophenyl)benzo[d]pyrrolo[2,1-b]thiazole-2,3-diyl)dimethanol (BO-1582) (0.25 g, 0.7 mmol) in anhydrous THF was treated with excess triethylamine (0.4 mL) followed by excess ethylisocyanate (0.23 g, 3.0 mmol). The reaction mixture was stirred at ambient temperature under an argon atmosphere. After being stirred overnight, the reaction mixture was evaporated to dryness in vacuo. The residue was recrystallized from ethanol to give (1-(4-chlorophenyl)benzo[d]pyrrolo[2,1-b]thiazole-2,3-diyl)bis(methylene)bis(ethylcarbamate) (BO-1596), 0.28 g (78%); mp 190-191° C. $^1$H NMR (DMSO-$d_6$) δ 1.00 (6H, t, J=7.2 Hz, 2×Me), 2.99 (4H, q, J=7.2 Hz, $CH_2$), 4.83 (2H, s, $CH_2$), 5.13 (2H, s, $CH_2$), 6.87-6.89 (1H, m, ArH), 7.07-7.14 (2H, brs, exchangeable, NH), 7.21-7.29 (2H, m, 2×ArH), 7.55 (2H, d, J=8.4 Hz, 2×ArH), 7.63 (2H, d, J=8.4 Hz, 2×ArH), 7.88-7.90

(1H, m, ArH). Anal. Calcd. for ($C_{24}H_{24}ClN_3O_4S$): C, 59.31; H, 4.98; N, 8.65; S, 6.60. Found: C, 59.44; H, 4.95; N, 8.52; S, 6.72.

5) (1-(4-Chlorophenyl)benzo[d]pyrrolo[2,1-b]thiazole-2,3-diyl)bis(methylene)bis(iso-propylcarbamate) (BO-1600)

A solution of (1-(4-chlorophenyl)benzo[d]pyrrolo[2,1-b]thiazole-2,3-diyl)dimethanol (BO-1582) (0.17 g, 0.5 mmol) in anhydrous THF was treated with excess triethylamine (0.3 mL) followed by excess isopropylisocyanate (0.17 g, 2.0 mmol). The reaction mixture was stirred at ambient temperature under an argon atmosphere. After being stirred overnight, the reaction mixture was evaporated to dryness in vacuo. The residue was recrystallized from ethanol to give (1-(4-chlorophenyl)benzo[d]pyrrolo[2,1-b]thiazole-2,3-diyl)bis(methylene)bis(iso-propylcarbamate) (BO-1600), 0.2 g (78%); mp 171-172° C. $^1$H NMR (DMSO-$d_6$) δ 1.04 (12H, d, J=6.4 Hz, 4×Me), 3.59 (2H, m, CH), 4.82 (2H, s, $CH_2$), 5.12 (2H, s, $CH_2$), 6.87-6.89 (1H, m, ArH), 6.97-7.05 (2H, brs, exchangeable, NH), 7.20-7.28 (2H, m, 2×ArH), 7.54 (2H, d, J=8.4 Hz, 2×ArH), 7.63 (2H, d, J=8.4 Hz, 2×ArH), 7.87-7.89 (1H, m, ArH). Anal. Calcd. for ($C_{26}H_{28}ClN_3O_4S.0.5H_2O$): C, 59.70; H, 5.59; N, 8.03; S, 6.13. Found: C, 59.38; H, 5.32; N, 7.87; S, 6.50.

Example 4

Synthesis of (1-(4-methoxyphenyl)benzo[d]pyrrolo[2,1-b]thiazole-2,3-diyl)dimethanol (BO-1646), (1-(4-methoxyphenyl)benzo[d]pyrrolo[2,1-b]thiazole-2,3-diyl)bis(methylene)bis(ethylcarbamate) (BO-1647), and (1-(4-methoxyphenyl)benzo[d]pyrrolo[2,1-b]thiazole-2,3-diyl)bis(methylene)bis(iso-propylcarbamate) (BO-1648)

1) 3-(4-Methoxybenzoyl)-2,3-dihydrobenzo[d]thiazole-2-carbonitrile 4-methoxybenzoylchloride (7.0 g, 41.0 mmol) was added dropwise to a stirring solution of benzothiazole (5.4 g, 40.0 mmol) in dichloromethane (40 mL) under argon atmosphere. A catalytic amount of $AlCl_3$ and trimethylsilylcyanide (4.1 g, 42.0 mmol) were than added into the reaction mixture. After being stirred for 14 h at room temperature, the reaction mixture was evaporated to dryness in vacuo and the residue was triturated with ether to give 3-(4-methoxybenzoyl)-2,3-dihydrobenzo[d]thiazole-2-carbonitrile, 8.2 g (70%); mp 122-123° C. (Lit.$^{21}$ 122-123° C.). $^1$H NMR (DMSO-$d_6$) δ 3.82 (3H, s, MeO), 6.72 (1H, brs, C2-H), 6.84 (1H, s, ArH), 7.01-7.14 (4H, m, 4×ArH), 7.52-7.55 (3H, m, 3×ArH).

2) Dimethyl 1-(4-methoxyphenyl)benzo[d]pyrrolo[2,1-b]thiazole-2,3-dicarboxylate To a solution of 3-(4-methoxybenzoyl)-2,3-dihydrobenzo[d]thiazole-2-carbonitrile (5.3 g, 17.9 mmol) in dichloromethane (50 mL) was added dropwise 5 mL of tetrafluoroboric acid ($HBF_4$). The solution was stirred for 3 h at room temperature. The brown precipitates appeared were collected by filtration and the filter cake was washed with ether. The solid salt was added to a solution of dimethyl acetylenedicarboxylate (7.6 g, 54.0 mmol) in DMF (40 mL) and then warmed at 35° C. for 14 h. The reaction mixture was concentrated in vacuo and the residue was crystallized from methanol to give dimethyl 1-(4-methoxyphenyl)benzo[d]pyrrolo[2,1-b]thiazole-2,3-dicarboxylate 1.7 g (24%); mp 167-168° C. $^1$H NMR (DMSO-$d_6$) δ 3.63 (3H, s, COOMe), 3.82 (3H, s, COOMe), 3.86 (3H, s, Me), 6.84-6.86 (1H, m, ArH), 7.12 (2H, d, J=8.4 Hz, 2×ArH), 7.28-7.32 (1H, m, ArH), 7.37-7.40 (1H, m, ArH), 7.48 (2H, d, J=8.4 Hz, 2×ArH), 8.03-8.05 (1H, m, ArH). Anal. Calcd. for ($C_{21}H_{17}NO_5S$): C, 63.79; H, 4.33; N, 3.54; S, 8.11.
Found: C, 63.81; H, 4.33; N, 3.55; S, 8.10.

3) (1-(4-Methoxyphenyl)benzo[d]pyrrolo[2,1-b]thiazole-2,3-diyl)dimethanol (BO-1646)

A solution of 1-(4-methoxyphenyl)benzo[d]pyrrolo[2,1-b]thiazole-2,3-dicarboxylate (1.7 g, 4.3 mmol) in anhydrous dichloromethane (30 mL) was added dropwise to a stirred mixture of lithium aluminum hydride (0.4 g, 10.0 mmol) in anhydrous ether (20 mL) at −5° C. to 0° C. The reaction mixture was allowed to stir at this temperature for 20 min. The excess hydride was decomposed by adding water (1 mL) followed by $NH_4OH$ (1 mL) and water (1 mL) at −5° C. to 0° C. The mixture was filtered through a pad of Celite, washed with several times with dichloromethane. The combined filtrate and washings were washed successively with water and brine solution. The organic layer was dried ($Na_2SO_4$) and concentrated to dryness in vacuo. The residue was crystallized from ethanol to give (1-(4-methoxyphenyl)benzo[d]pyrrolo[2,1-b]thiazole-2,3-diyl)-dimethanol (BO-1646), 1.3 g (91%); mp 156-157° C. $^1$H NMR (DMSO-$d_6$) δ 3.85 (3H, s, MeO), 4.22 (2H, d, J=4.8 Hz, $CH_2$), 4.66 (3H, m, $CH_2$ and exchangeable OH), 5.09 (1H, t, J=4.8 Hz, exchangeable, OH), 6.85-6.87 (1H, m, ArH), 7.08-7.19 (4H, m, 4×ArH), 7.39-7.42 (2H, m, 2×ArH), 7.76-7.79 (1H, m, ArH). Anal. Calcd. for ($C_{19}H_{17}NO_3S$): C, 67.24; H, 5.05; N, 4.13; S, 9.45. Found: C, 67.54; H, 5.00; N, 4.00; S, 9.30.

4) (1-(4-Methoxyphenyl)benzo[d]pyrrolo[2,1-b]thiazole-2,3-diyl)bis(methylene)bis(ethylcarbamate) (BO-1647)

A solution of (1-(4-methoxyphenyl)benzo[d]pyrrolo[2,1-b]thiazole-2,3-diyl)dimethanol (BO-1646) (0.2 g, 0.6 mmol) in anhydrous THF was treated with excess triethylamine (0.3 mL) followed by excess ethylisocyanate (0.17 g, 2.4 mmol). The reaction mixture was stirred at ambient temperature under an argon atmosphere. After the completion of the reaction, the reaction mixture was evaporated to dryness in vacuo. The residue was recrystallized from ethanol to give (1-(4-methoxyphenyl)benzo[d]pyrrolo[2,1-b]thiazole-2,3-diyl)bis(methylene)bis(ethylcarbamate) (BO-1647), 0.24 g (85%); mp 146-147° C. $^1$H NMR (DMSO-$d_6$) δ 1.00 (6H, t, J=7.2 Hz, 2×Me), 2.99 (4H, q, J=7.2 Hz, $CH_2$), 3.87 (3H, s, OMe), 4.80 (2H, s, $CH_2$), 5.11 (2H, s, $CH_2$), 6.83-6.85 (1H, m, ArH), 7.04-7.10 (2H, brs, exchangeable, NH), 7.11-7.13 (2H, m, 2×ArH), 7.18-7.26 (2H, m, 2×ArH), 7.41-7.43 (2H, m, 2×ArH), 7.84-7.86 (1H, m, ArH). Anal. Calcd. for ($C_{25}H_{27}N_3O_5S$): C, 62.35; H, 5.65; N, 8.73; S, 6.66. Found: C, 62.19; H, 5.55; N, 7.03; S, 8.75.

5) (1-(4-Methoxyphenyl)benzo[d]pyrrolo[2,1-b]thiazole-2,3-diyl)bis(methylene)bis(iso-propylcarbamate) (BO-1648)

A solution of (1-(4-methoxyphenyl)benzo[d]pyrrolo[2,1-b]thiazole-2,3-diyl)dimethanol (BO-1646) (0.25 g, 0.7 mmol) in anhydrous THF was treated with excess triethylamine (0.4 mL) followed by excess isopropylisocyanate (0.24 g, 2.8 mmol). The reaction mixture was stirred at ambient temperature under an argon atmosphere. After the completion of the reaction, the reaction mixture was evaporated to dryness in vacuo. The residue was recrystallized from ethanol to give (1-(4-methoxyphenyl)benzo[d]pyrrolo[2,1-b]thiazole-2,3-diyl)bis(methylene)bis(iso-propyl-carbamate) (BO-1648), 0.32 g (86%); mp 141-142° C. $^1$H NMR (DMSO-$d_6$) δ 1.04 (12H, d, J=6.6 Hz, 4×Me), 3.59 (2H, m, CH), 3.87 (3H, s, MeO), 4.81 (2H, s, CH$_2$), 5.11 (2H, s, CH$_2$), 6.83-6.85 (1H, m, ArH), 6.97-7.04 (2H, brs, exchangeable, NH), 7.12 (2H, d, J=8.4 Hz, 2×ArH), 7.17-7.25 (2H, m, 2×ArH), 7.42 (2H, d, J=8.4 Hz, 2×ArH), 7.84-7.86 (1H, m, ArH). Anal. Calcd. for (C$_{27}$H$_{31}$N$_3$O$_5$S): C, 63.63; H, 6.13; N, 8.25; S, 6.29. Found: C, 63.38; H, 6.06; N, 8.05; S, 6.61.

By following the same synthetic route described above, compounds of Formula I and Formula II as shown in Table 1 and 2 were synthesized.

Synthesis of
1,2-bis(hydroxymethyl)indolizino[6,7-b]indoles
(Formula III) and their bis(alkylcarbamates)
derivatives (Formula IV)

Example 5

Synthesis of [3,6-dimethyl-6,11-dihydro-5H-indolizino[6,7-b]indole-1,2-diyl]dimethanol (BO-1922), [3,6-dimethyl-6,11-dihydro-5H-indolizino[6,7-b]indole-1,2-diyl]bis(methylene)-bis(ethylcarbamate) (BO-1923), and [3,6-dimethyl-6,11-dihydro-5H-indolizino[6,7-b]-indole-1,2-diyl]bis(methylene)bis(iso-propylcarbamate) (BO-1924)

1) 1,2,3,4-Tetrahydro-pyrido[3,4-b]indole-3-carboxylic acid

To a mixture of 0.1 NH$_2$SO$_4$ (150 mL) and 37% formaldehyde (80 mL) was added portionwise L-tryptophane (50 g, 245 mmol) with stirring. After being stirred for 4 h at room temperature, the white solid separated out was collected by filtration. The solid cake was washed with water and dried to give 1,2,3,4-tetrahydro-pyrido[3,4-b]indole-3-carboxylic acid, 41 g, (78%); mp 275-276° C. (lit.[18] mp 280-282° C.). $^1$H NMR (DMSO-$d_6$) δ 2.84 (1H, m, CH$_2$), 3.16 (1H, m, CH$_2$), 3.66 (1H, m, CH$_2$), 4.23 (1H, m, CH$_2$), 4.38 (1H, m, CH), 6.98-7.02 (1H, m, ArH), 7.13-7.16 (1H, m, ArH), 7.32-7.34 (1H, m, ArH), 7.45-7.48 (1H, m, ArH), 11.03 (1H, brs, exchangeable, NH).

2) Dimethyl 3-methyl-6,11-dihydro-5H-indolizino[6,7-b]indole-1,2-dicarboxylate

Dimethyl acetylenedicarboxylate (8.4 g, 59.5 mmol) was added into a mixture of 1,2,3,4-tetrahydro-pyrido[3,4-b]indole-3-carboxylic acid (10 g, 39.6 mmol) in acetic anhydride (70 mL). The reaction mixture was heated at 70° C. with stirring for 2 h and then evaporated in vacuo to dryness. The residue was recrystallized from MeOH to give dimethyl 3-methyl-6,11-dihydro-5H-indolizino[6,7-b]indole-1,2-dicarboxylate, 11.5 g (86%); mp 252-253° C. (lit.[20] mp 255-260° C.). $^1$H NMR (DMSO-$d_6$) δ 2.43 (3H, s, Me), 3.73 (3H, s, COOMe), 3.75 (3H, s, COOMe), 4.16 (2H, s, CH$_2$), 5.21 (2H, s, CH$_2$), 7.02-7.06 (1H, m, ArH), 7.11-7.14 (1H, m, ArH), 7.39 (1H, d, J=8.0 Hz, ArH), 7.52 (1H, d, J=7.8 Hz, ArH), 11.12 (1H, s, exchangeable, NH).

3) Dimethyl 3,6-dimethyl-6,11-dihydro-5H-indolizino[6,7-b]indole-1,2-dicarboxylate To a suspension of NaH (0.63 g, 26.5 mmol) in dry DMF (150 ml) was added portionwise dimethyl 3-methyl-6,11-dihydro-5H-indolizino[6,7-b]indole-1,2-dicarboxylate (6 g, 17.7 mmol) at 0° C. to 5° C. After being stirred for 15 min, iodomethane (2.5 g, 17.7 mmol) was added and the reaction mixture and was stirred for additional 1 h in an ice bath. After being stirred at room temperature for 9 h, methanol was added into the reaction mixture and then evaporated to dryness in vacuo. The residue was recrystallized from MeOH to give dimethyl 3,6-dimethyl-6,11-dihydro-5H-indolizino[6,7-b]indole-1,2-dicarboxylate, 5.8 g (94%); mp 240-241° C. $^1$H NMR (DMSO-$d_6$) δ 2.45 (3H, s, Me), 3.73 (6H, s, COOMe and Me), 3.74 (3H, s, COOMe), 4.16 (2H, t, J=3.4 Hz, CH$_2$), 5.27 (2H, t, J=3.4 Hz, CH$_2$), 7.05-7.09 (1H, m, ArH), 7.17-7.21 (1H, m, ArH), 7.48 (1H, d, J=8.2 Hz, ArH), 7.53 (1H, d, J=7.8 Hz, ArH). Anal. Calcd for (C$_{20}$H$_{20}$N$_2$O$_4$): C, 68.17; H, 5.72; N, 7.95. Found: C, 67.79; H, 5.73; N, 7.84.

4) [3,6-Dimethyl-6,11-dihydro-5H-indolizino[6,7-b]indole-1,2-diyl]dimethanol (BO-1922

A solution of dimethyl 3,6-dimethyl-6,11-dihydro-5H-indolizino[6,7-b]indole-1,2-dicarboxylate (3.5 g, 10.0 mmol) in anhydrous dichloromethane (35 mL) was added dropwise into a stirred suspension of LiAlH$_4$ (0.9 g, 25.0 mmol) in anhydrous diethyl ether (20 mL) at 0 to −5° C. The reaction mixture was further stirred for 15 min after the addition was completed. The excess hydride was destroyed by the sequential addition of water (1 mL), 15% aqueous NaOH (1 mL), and water (1 mL) at 0° C. The mixture was filtered through a pad of Celite, the solid residue was washed with dichloromethane. The combined filtrate and washings were evaporated to dryness in vacuo. The residue was triturated with ether to give [3,6-dimethyl-6,11-dihydro-5H-indolizino[6,7-b]indole-1,2-diyl]dimethanol (BO-1922), 2.3 g (79%); mp 200-201° C. $^1$H NMR (DMSO-$d_6$) δ 2.29 (3H, s, Me), 3.73 (3H, s, Me), 3.99 (2H, s, CH$_2$), 4.38 (4H, brs, CH$_2$ and exchangeable, OH), 4.44 (2H, s, CH$_2$), 5.13 (2H, s, CH$_2$), 7.05 (1H, t, J=7.4 Hz, ArH), 7.16 (1H, t, J=7.4 Hz, ArH), 7.46 (1H, d, J=7.8 Hz, ArH), 7.53 (1H, d, J=7.8 Hz, ArH). Anal. Calcd for (C$_{18}$H$_{20}$N$_2$O$_2$.0.5H$_2$O): C, 70.80; H, 6.93; N, 9.17. Found: C, 70.85; H, 6.65; N, 9.02.

5) [3,6-Dimethyl-6,11-dihydro-5H-indolizino[6,7-b]indole-1,2-diyl]bis(methylene)bis(ethyl carbamate) (BO-1923)

To a solution of [3,6-dimethyl-6,11-dihydro-5H-indolizino[6,7-b]indole-1,2-diyl]dimethanol (BO-1922) (0.29 g, 1 mmol) and triethylamine (0.3 mL) in anhydrous DMF was added ethylisocyanate (0.28 g, 4 mmol). The reaction mixture was stirred at ambient temperature for 12 h under an argon atmosphere. After the completion of the reaction, the reaction mixture was evaporated to dryness in vacuo. The residue was recrystallized from ethanol to give [3,6-dimethyl-6,11-dihydro-5H-indolizino[6,7-b]indole-1,2-diyl]bis(methylene)bis(ethylcarbamate) (BO-1923), 0.3 g (69%); mp 165-166° C. $^1$H NMR (DMSO-$d_6$) δ 0.98 (6H, t, J=6.9 Hz, 2×Me), 2.32 (3H, s, Me), 2.98 (4H, q, J=6.9 Hz, CH$_2$), 3.73 (3H, s, NMe), 4.04 (2H, s, CH$_2$), 4.94 (2H, s, CH$_2$), 4.98 (2H, s, CH$_2$), 5.17 (2H, s, CH$_2$), 6.88-6.91 (2H, brs, exchangeable, NH), 7.04-7.08 (1H, m, ArH), 7.15-7.19 (1H, m, ArH), 7.46-7.48 (1H, m, ArH), 7.52-7.54 (1H, m, ArH). Anal. Calcd for (C$_{24}$H$_{30}$N$_4$O$_4$): C, 65.73; H, 6.90; N, 12.78. Found: C, 65.53; H, 6.75; N, 12.44.

6) [3,6-Dimethyl-6,11-dihydro-5H-indolizino[6,7-b]indole-1,2-diyl]bis(methylene)bis-(isopropylcarbamate) (BO-1924)

To a solution of [3,6-dimethyl-6,11-dihydro-5H-indolizino[6,7-b]indole-1,2-diyl]dimethanol (BO-1922) (0.29 g, 1 mmol) and triethylamine (0.3 mL) in anhydrous DMF was added isopropylisocyanate (0.34 g, 4 mmol). The reaction mixture was stirred at ambient temperature for 12 h under an argon atmosphere. After the completion of the reaction, the reaction mixture was evaporated to dryness in vacuo. The residue was recrystallized from ethanol to give [3,6-dimethyl-6,11-dihydro-5H-indolizino[6,7-b]indole-1,2-diyl]bis(methylene)bis(iso-propylcarbamate) (BO-1924), 0.32 g (68%); mp 190-191° C. $^1$H NMR (DMSO-$d_6$) δ 1.02 (12H, d, J=6.4 Hz, 4×Me), 2.31 (3H, s, Me), 3.56 (2H, m, CH), 3.73 (3H, s, NMe), 4.03 (2H, s, $CH_2$), 4.94 (2H, s, $CH_2$), 4.98 (2H, s, $CH_2$), 5.16 (2H, s, $CH_2$), 6.81-6.83 (2H, brs, exchangeable, NH), 7.04-7.07 (1H, m, ArH), 7.15-7.18 (1H, m, ArH), 7.45-7.47 (1H, m, ArH), 7.52-7.54 (1H, m, ArH). Anal. Calcd for ($C_{26}H_{34}N_4O_4$): C, 66.93; H, 7.35; N, 12.01. Found: C, 66.79; H, 7.15; N, 11.73.

Example 6

By following the same synthetic route as that for BO-1922, BO-1923, and BO-1924, the following compounds were prepared.

[6-Ethyl-3-methyl-6,11-dihydro-5H-indolizino[6,7-b]indole-1,2-diyl]dimethanol (BO-1972), [6-ethyl-3-methyl-6,11-dihydro-5H-indolizino[6,7-b]indole-1,2-diyl]bis(methylene)bis(ethylcarbamate) (BO-1973), and [6-ethyl-3-methyl-6,11-dihydro-5H-indolizino[6,7-b]indole-1,2-diyl]bis(methylene)bis(iso-propylcarbamate) (BO-1974)

1) Dimethyl 6-ethyl-3-methyl-6,11-dihydro-5H-indolizino[6,7-b]indole-1,2-dicarboxylate This compound was prepared from dimethyl 3-methyl-6,11-dihydro-5H-indolizino[6,7-b]indole-1,2-dicarboxylate (5.1 g, 15 mmol), NaH (0.54 g, 22.5 mmol) and iodoethane (2.3 g, 15 mmol). Yield 5.1 g (92%); mp 202-203° C. $^1$H NMR (DMSO-$d_6$) δ 1.29 (3H, t, J=6.9 Hz, Me), 2.46 (3H, s, Me), 3.73 (3H, s, COOMe), 3.74 (3H, s, COOMe), 4.17 (2H, s, $CH_2$), 4.20 (2H, q, J=6.9 Hz, $CH_2$), 5.29 (2H, s, $CH_2$), 7.05-7.09 (1H, m, ArH), 7.16-7.20 (1H, m, ArH), 7.49-7.51 (1H, m, ArH), 7.53-7.55 (1H, m, ArH). Anal. Calcd for ($C_{21}H_{22}N_2O_4$): C, 68.84; H, 6.05; N, 7.65. Found: C, 68.46; H, 6.06; N, 7.59.

2) [6-Ethyl-3-methyl-6,11-dihydro-5H-indolizino[6,7-b]indole-1,2-diyl]dimethanol (BO-1972)

Compound BO-1972 was prepared from dimethyl 6-ethyl-3-methyl-6,11-dihydro-5H-indolizino-[6,7-b]indole-1,2-dicarboxylate (3.6 g, 10 mmol) and LiAlH$_4$ (0.92 g, 25 mmol). Yield 2.5 g (80%); mp 216-217° C. $^1$H NMR (DMSO-$d_6$) δ 1.29 (3H, t, J=7.1 Hz, Me), 2.30 (3H, s, Me), 4.00 (2H, s, $CH_2$), 4.21 (2H, q, J=7.1 Hz, $CH_2$), 4.38 (3H, br s, $CH_2$ and exchangeable, OH), 4.44 (3H, br s, $CH_2$ and exchangeable, OH), 5.13 (2H, s, $CH_2$), 7.04-7.07 (1H, m, ArH), 7.14-7.18 (1H, m, ArH), 7.47-7.49 (1H, m, ArH), 7.53-7.55 (1H, m, ArH). Anal. Calcd for ($C_{19}H_{22}N_2O_2$): C, 73.52; H, 7.14; N, 9.03. Found: C, 73.68; H, 6.93; N, 8.66.

3) [6-Ethyl-3-methyl-6,11-dihydro-5H-indolizino[6,7-b]indole-1,2-diyl]bis(methylene)bis(ethylcarbamate) (BO-1973)

Compound BO-1973 was prepared from [6-ethyl-3-methyl-6,11-dihydro-5H-indolizino-[6,7-b]indole-1,2-diyl] dimethanol (0.62 g, 2 mmol), Et$_3$N (0.6 mL), and ethylisocyanate (0.56 g, 8 mmol). Yield, 0.52 g (57%); mp 178-179° C. $^1$H NMR (DMSO-$d_6$) δ 0.98 (6H, t, J=7.1 Hz, 2×Me), 1.29 (3H, t, J=7 Hz, Me), 2.33 (3H, s, Me), 2.97 (4H, q, J=7.1 Hz, $CH_2$), 4.04 (2H, s, $CH_2$), 4.21 (2H, q, J=7 Hz, $CH_2$), 4.94 (2H, s, $CH_2$), 4.99 (2H, s, $CH_2$), 5.17 (2H, s, $CH_2$), 6.89 (2H, br s, exchangeable, NH), 7.04-7.08 (1H, m, ArH), 7.15-7.18 (1H, m, ArH), 7.47-7.49 (1H, m, ArH), 7.52-7.54 (1H, m, ArH). Anal. Calcd for ($C_{25}H_{32}N_4O_4$.0.5$H_2O$): C, 65.06; H, 7.21; N, 12.14. Found: C, 64.71; H, 7.09; N, 12.03.

4) [6-Ethyl-3-methyl-6,11-dihydro-5H-indolizino[6,7-b]indole-1,2-diyl]bis(methylene)-bis(iso-propylcarbamate) (BO-1974)

Compound BO-1974 was prepared from [6-ethyl-3-methyl-6,11-dihydro-5H-indolizino[6,7-b]indole-1,2-diyl] dimethanol (0.62 g, 2 mmol), Et$_3$N (0.6 mL), and isopropylisocyanate (0.68 g, 8 mmol). Yield, 0.61 g (63%); mp 219-220° C. $^1$H NMR (DMSO-$d_6$) δ 1.01 (12H, d, J=6.4 Hz, 4×Me), 1.29 (3H, t, J=7 Hz, Me), 2.33 (3H, s, Me), 3.57 (2H, m, CH), 4.04 (2H, s, $CH_2$), 4.21 (2H, q, J=7 Hz, $CH_2$), 4.94 (2H, s, $CH_2$), 4.99 (2H, s, $CH_2$), 5.17 (2H, s, $CH_2$), 6.82 (2H, br s, exchangeable, NH), 7.04-7.08 (1H, m, ArH), 7.15-7.18 (1H, m, ArH), 7.45-7.49 (1H, m, ArH), 7.52-7.54 (1H, m, ArH). Anal. Calcd for ($C_{27}H_{36}N_4O_4$): C, 67.48; H, 7.55; N, 11.66. Found: C, 67.26; H, 7.59; N, 11.54.

Example 7

Synthesis of (3-(4-chlorophenyl)-6-methyl-6,11-dihydro-5H-indolizino[6,7-b]indole-1,2-diyl) dimethanol (BO-1934), [3-(4-chlorophenyl)-6-methyl-6,11-dihydro-5H-indolizino[6,7-b]-indole-1,2-diyl]bis(methylene)bis (ethylcarbamate) (BO-1935), and [3-(4-chlorophenyl)-6-methyl-6,11-dihydro-5H-indolizino[6,7-b]indole-1,2-diyl]bis(methylene) (isopropylcarbamate) (BO-1936).

1) Methyl 1,2,3,4-tetrahydro-9H-pyrido[3,4-h]indole-3-carboxylate

A mixture of L-tryptophane methyl ester (25.4 g, 100 mmol) and 37% formaldehyde solution (12.5 mL) in aqueous methanol (170 mL; $H_2O$:MeOH, v/v 10:1) was stirred at room temperature for 5 h. The reaction mixture was evaporated to dryness in vacuo. The residue was basified with sodium bicarbonate to give methyl 1,2,3,4-tetrahydro-9H-pyrido[3,4-b]indole-3-carboxylate, 14.4 g (63%); mp 161-162° C. (lit.[19] mp 164-165° C.). $^1$H NMR (DMSO-$d_6$) δ 2.78 (1H, m, $CH_2$), 2.98 (1H, m, $CH_2$), 3.66 (3H, s, COOMe), 3.85 (1H, m, CH), 4.02 (2H, q, J=15.8 Hz, $NCH_2$), 6.92-6.96 (1H, m, ArH), 7.00-7.04 (1H, m, ArH), 7.27-7.29 (1H, m, ArH), 7.37-7.39 (1H, m, ArH), 10.78 (1H, s, exchangeable NH).

2) Methyl 2-(4-chlorobenzoyl)-1,2,3,4-tetrahydro-9H-pyrido[3,4-h]indole-3-carboxylate A mixture of methyl 1,2,3,4-tetrahydro-9H-pyrido[3,4-b]indole-3-carboxylate (6.9 g, 30 mmol), benzoylchloride (4.2 g, 30 mmol) and triethylamine (4.8 mL) in anhydrous THF (150 mL) was refluxed for 9 h. It was concentrated and diluted with water. The solid precipitated was collected by filtration, the solid cake was washed successively with water and hexane and dried to give methyl 2-(4-chlorobenzoyl)-1,2,3,4-tetrahydro-9H-pyrido[3,4-b]indole-3-carboxylate, 9.0 g (82%); mp 243-244° C. (lit.[19] mp 245-246° C.). $^1$H NMR (DMSO-$d_6$) δ 3.10 (1H, m, $CH_2$), 3.35 (1H, m, $CH_2$), 3.55 and 3.65 (3H, s, COOMe), 4.41 and 5.18 (1H, d, J=17.4 Hz, NCH$_2$), 4.51 and 4.64 (1H, d, J=16.4 Hz, NCH$_2$), 4.88 and 5.82 (1H, d, J=5.4 Hz, CH), 6.96-6.99 (1H, m, ArH), 7.03-7.08 (1H, m, ArH), 7.25-7.32 (1H, m, ArH), 7.42-7.60 (5H, m, 5×ArH), 10.65 and 10.95 (1H, s, exchangeable NH).

3) 2-(4-Chlorobenzoyl)-9-methyl-1,2,3,4-tetrahydro-pyrido[3,4-b]indole-3-carboxylic acid To a suspension of NaH (0.96 g, 40.0 mmol) in dry DMF (150 ml) was added portionwise methyl 2-(4-chlorobenzoyl)-1,2,3,4-tetrahydro-9H-pyrido[3,4-b]indole-3-carboxylate (7.3 g, 20.0 mmol) at 0° C. to 5° C. After being stirred for 15 min, iodomethane (2.8 g, 20.0 mmol) was added and the reaction mixture was stirred for additional 1 h in an ice bath. The mixture was then stirred at room temperature for 9 h. The excess of hydride was decomposed with methanol and the reaction mixture was then evaporated to dryness in vacuo. The residue was recrystallized from MeOH to give 2-(4-chlorobenzoyl)-9-methyl-1,2,3,4-tetrahydro-pyrido[3,4-b]indole-3-carboxylic acid, 5.4 g (74%); mp 262-263° C. $^1$H NMR (Acetic acid-d$_4$) δ 3.18 (1H, m, CH$_2$), 3.56 (1H, m, CH$_2$), 3.45 and 3.68 (3H, s, NMe), 4.64 and 5.40 (1H, d, J=15.8 Hz, NCH$_2$), 4.70 and 4.93 (1H, d, J=17.1 Hz, NCH$_2$), 5.02 and 6.12 (1H, d, J=5.4 Hz, CH), 7.04-7.07 (1H, m, ArH), 7.15-7.18 (1H, m, ArH), 7.31-7.33 (1H, m, ArH), 7.45-7.47 (1H, m, ArH), 7.50-7.55 (3H, m, 3×ArH), 7.59-7.61 (1H, m, ArH). Anal. Calcd for (C$_{20}$H$_{17}$ClN$_2$O$_3$): C, 65.13; H, 4.65; N, 7.60. Found: C, 64.77; H, 4.79; N, 7.68.

4) Dimethyl 3-(4-chlorophenyl)-6-methyl-6,11-dihydro-5H-indolizino[6,7-b]indole-1,2-dicarboxylate A mixture of 2-(4-chlorobenzoyl)-9-methyl-1,2,3,4-tetrahydropyrido[3,4-b]indole-3-carboxylic acid (4 g, 10.8 mmol), DMAD (2.3 g, 16.3 mmol) in AC$_{20}$ (30 mL) was heated at 80° C. for 2 h. The reaction mixture evaporated in vacuo to dryness. The residue was recrystallized from MeOH to give dimethyl 3-(4-chlorophenyl)-6-methyl-6,11-dihydro-5H-indolizino[6,7-b]indole-1,2-dicarboxylate, 3.5 g, (72%); mp 264-265° C. $^1$H NMR (DMSO-d$_6$) δ 3.60 (6H, s, 2×COOMe), 3.78 (3H, s, NMe), 4.30 (2H, s, CH$_2$), 5.18 (2H, s, CH$_2$), 7.06-7.10 (1H, m, ArH), 7.17-7.20 (1H, m, ArH), 7.45-7.47 (1H, m, ArH), 7.54-7.59 (5H, m, 5×ArH). Anal. Calcd for (C$_{25}$H$_{21}$ClN$_2$O$_4$): C, 66.89; H, 4.72; N, 6.24. Found: C, 66.82; H, 4.63; N, 6.24.

5) (3-(4-Chlorophenyl)-6-methyl-6,11-dihydro-5H-indolizino[6,7-b]indole-1,2-diyl)-dimethanol (BO-1934)

A solution of dimethyl 3-(4-chlorophenyl)-6-methyl-6,11-dihydro-5H-indolizino[6,7-b]indole-1,2-dicarboxylate (3.2 g, 7 mmol) in anhydrous dichloromethane (35 mL) was added dropwise into a stirred suspension of LiAlH$_4$ (0.6 g, 17.8 mmol) in anhydrous diethyl ether (20 mL) at 0 to −5° C. The reaction mixture was further stirred for 15 min after the addition was completed. The excess hydride was destroyed by the sequential addition of water (1 mL), 15% aqueous NaOH (1 mL), and water (1 mL) at 0° C. The mixture was filtered through a pad of Celite and the solid was washed with dichloromethane. The combined filtrate and washings were evaporated to dryness in vacuo. The residue was triturated with ether to give (3-(4-chlorophenyl)-6-methyl-6,11-dihydro-5H-indolizino[6,7-b]indole-1,2-diyl)-dimethanol (BO-1934), 2.2 g (77%); mp 238-239° C. $^1$H NMR (DMSO-d$_6$) δ 3.62 (3H, s, Me), 4.10 (2H, s, CH$_2$), 4.29 (2H, m, CH$_2$), 4.55 (2H, s, CH$_2$) 4.59 (2H, brs, exchangeable, 2×OH), 5.16 (2H, s, CH$_2$), 7.04-7.08 (1H, m, ArH), 7.14-7.18 (1H, m, ArH), 7.43-7.45 (1H, m, ArH), 7.53-7.59 (5H, m, 5×ArH). Anal. Calcd for (C$_{23}$H$_{21}$ClN$_2$O$_2$.0.5H$_2$O): C, 68.74; H, 5.52; N, 6.97. Found: C, 68.72; H, 5.16; N, 6.94.

6) [3-(4-Chlorophenyl)-6-methyl-6,11-dihydro-5H-indolizino[6,7-b]indole-1,2-diyl]bis-(methylene)bis (ethylcarbamate) (BO-1935)

To a solution of (3-(4-chlorophenyl)-6-methyl-6,11-dihydro-5H-indolizino[6,7-b]indole-1,2-diyl)-dimethanol (BO-1934) (0.4 g, 1 mmol) and triethylamine (0.4 mL) in anhydrous DMF was added ethylisocyanate (0.28 g, 4 mmol). The reaction mixture was stirred at ambient temperature for 12 h under an argon atmosphere. After the completion of the reaction, the reaction mixture was evaporated to dryness in vacuo. The residue was recrystallized from ethanol to give [3-(4-chlorophenyl)-6-methyl-6,11-dihydro-5H-indolizino[6,7-b] indole-1,2-diyl]bis-(methylene)bis(ethylcarbamate) (BO-1935), 0.31 g (58%); mp 176-177° C. $^1$H NMR (DMSO-d$_6$) δ 0.98 (6H, t, J=6.4 Hz, 2×Me), 2.98 (4H, q, J=6.4 Hz, CH$_2$), 3.60 (3H, s, NMe), 4.13 (2H, s, CH$_2$), 4.80 (2H, s, CH$_2$), 5.07 (2H, s, CH$_2$), 5.15 (2H, s, CH$_2$), 6.96-6.98 (2H, brs, exchangeable, NH), 7.04-7.08 (1H, m, ArH), 7.14-7.18 (1H, m, ArH), 7.43-7.45 (1H, m, ArH), 7.54-7.60 (5H, m, 5×ArH). Anal. Calcd for (C$_{29}$H$_{31}$ClN$_4$O$_4$.0.5H$_2$O): C, 64.02; H, 5.93; N, 10.30. Found: C, 63.97; H, 6.01; N, 10.29.

7) [3-(4-Chlorophenyl)-6-methyl-6,11-dihydro-5H-indolizino[6,7-b]indole-1,2-diyl]bis-(methylene) (isopropylcarbamate) (BO-1936)

To a solution of (3-(4-chlorophenyl)-6-methyl-6,11-dihydro-5H-indolizino[6,7-b]indole-1,2-diyl)-dimethanol (BO-1934) (0.4 g, 1 mmol) and triethylamine (0.4 mL) in anhydrous DMF was added isopropylisocyanate (0.34 g, 4 mmol). The reaction mixture was stirred at ambient temperature for 12 h under an argon atmosphere. After the completion of the reaction, the reaction mixture was evaporated to dryness in vacuo. The residue was recrystallized from ethanol to give [3-(4-chlorophenyl)-6-methyl-6,11-dihydro-5H-indolizino [6,7-b]indole-1,2-diyl]bis-(methylene) (iso-propylcarbamate) (BO-1936), 0.34 g (60%); mp 195-196° C. $^1$H NMR (DMSO-d$_6$) δ 1.02 (12H, d, J=6.4 Hz, 4×Me), 3.57 (2H, m, CH), 3.61 (3H, s, NMe), 4.14 (2H, s, CH$_2$), 4.81 (2H, s, CH$_2$), 5.08 (2H, s, CH$_2$), 5.16 (2H, s, CH$_2$), 6.87-6.90 (2H, brs, exchangeable, NH), 7.05-7.09 (1H, m, ArH), 7.15-7.19 (1H, m, ArH), 7.44-7.46 (1H, m, ArH), 7.54-7.58 (5H, m, 5×ArH). Anal. Calcd for (C$_{31}$H$_{35}$ClN$_4$O$_4$.0.5H$_2$O): C, 65.08; H, 6.34; N, 9.79. Found: C, 64.94; H, 6.21; N, 9.73.

By following the same synthetic route as described above, compounds of Formula III and Formula IV as shown in Table 3 and 4 were synthesized.

Biological Results

In Vitro Cytotoxicity Against Human Lymphoblastic Leukemia and Solid Tumors

Table 5 shows the cytotoxicity of the compounds disclosed herein in inhibiting tumor cell growth in cell culture. The IC$_{50}$ is defined by the concentration required to inhibit tumor cell growth by 50%. It demonstrated that these agents exhibited potent cytotoxicity against human lymphoblastic leukemia (CCRF/CEM) and its drug-resistant sublines (resistant to vinblastine and taxol, CCRF-CEM/VBL and CCRF-CEM/taxol, respectively) as shown in Table 5. The growth inhibition of the compounds disclosed herein against human solid tumors (e.g. breast MX-1, colon HCT-116, carcinoma HCT-116, prostate PC3, lung H1299, glioma U87, and oral OECM1) cell growth in vitro with submicromolar or micromolar IC$_{50}$ values (Table 6) were observed. Table 7 shows the anti-proliferative activity of 2,3-bis(hydroxymethyl)-5H-indolizino[6,7-b]-indole and their bis(alkylcarbamate) derivatives against human lymphoblastic leukemia (CCRF-CEM) and solid tumor (e.g. MX-1, HCT-116, PC3, H1299, U87, and OECM1 tumor cell lines) cell growth in vitro. The results demonstrated that the newly invented compounds exhibit significant anti-proliferative against various tumor cell growth in vitro and have little or no cross-resistance to either Taxol or Vinblastine. It suggested that analogues disclosed herein are effective against multiple drug resistant tumors.

TABLE 5

The cytotoxicity of newly synthesized 2,3-bis(hydroxymethyl)benzo[d]-pyrrolo[2,1-b]thiazole and their bis(alkylcarbamate) derivatives against human lymphoblastic leukemia (CCRF-CEM), its drug-resistant sublines (CCRF-CEM/Taxol and CCRF-CEM/VBL).

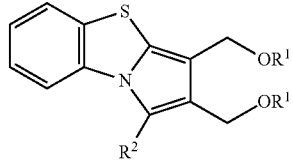

| Compd. | $R^1$ | $R^2$ | Cell Growth inhibition (IC$_{50}$ μM) | | |
|---|---|---|---|---|---|
| | | | CCRF-CEM | CCRF-CEM/Taxol[a] | CCRF-CEM/VBL[a] |
| 18a (BO-1595) | H | Me | 0.97 ± 0.03 | 1.88 ± 0.007 [1.93×][b] | 1.86 ± 0.010 [1.91×][b] |
| 19a (BO-1653) | CONHEt | Me | 0.33 ± 0.01 | 0.45 ± 0.013 [1.30×] | 0.43 ± 0.003 [1.30×] |
| 20a (BO-1652) | CONH-i-Pr | Me | 0.13 ± 0.01 | 0.22 ± 0.002 [1.69×] | 0.25 ± 0.01 [1.92×] |
| 18b (BO-1592) | H | 4'-F—C$_6$H$_4$ | 1.06 ± 0.04 | 2.56 ± 0.012 [2.41×] | 3.72 ± 0.175 [3.50×] |
| 19b (BO-1593) | CONHEt | 4'-F—C$_6$H$_4$ | 0.07 ± 0.0002 | 0.38 ± 0.002 [5.42×] | 0.45 ± 0.033 [6.42×] |
| 20b (BO-1597) | CONH-i-Pr | 4'-F—C$_6$H$_4$ | 0.05 ± 0.001 | 0.16 ± 0.007 [3.20×] | 0.19 ± 0.003 [3.80×] |
| 18c (BO-1582) | H | 4'-Cl—C$_6$H$_4$ | 2.61 ± 0.03 | 5.22 ± 0.026 [2.00×] | 4.09 ± 0.025 [1.56×] |
| 19c (BO-1596) | CONHEt | 4'-Cl—C$_6$H$_4$ | 0.21 ± 0.01 | 0.32 ± 0.003 [1.52×] | 0.39 ± 0.012 [1.85×] |
| 20c (BO-1600) | CONH-i-Pr | 4'-Cl—C$_6$H$_4$ | 0.08 ± 0.0003 | 0.39 ± 0.004 [4.87×] | 0.42 ± 0.001 [5.25×] |
| 18d (BO-1601) | H | 3',4'-F—C$_6$H$_3$ | 0.19 ± 0.02 | 0.19 ± 0.004 [100×] | 0.28 ± 0.006 [1.47×] |
| 19d (BO-1602) | CONHEt | 3',4'-F—C$_6$H$_3$ | 0.21 ± 0.01 | 0.34 ± 0.008 [1.61×] | 0.31 ± 0.002 [1.47×] |
| 20d (BO-1635) | CONH-i-Pr | 3',4'-F—C$_6$H$_3$ | 0.33 ± 0.001 | 0.19 ± 0.004 [0.57×] | 0.30 ± 0.001 [0.90×] |
| 18g (BO-1646) | H | 4'-MeO—C$_6$H$_4$ | 1.13 ± 0.09 | 2.17 ± 0.02 [1.9×] | 2.63 ± 0.031 [2.30×] |
| 19g (BO-1647) | CONHEt | 4'-MeO—C$_6$H$_4$ | 0.19 ± 0.002 | 0.37 ± 0.001 [1.90×] | 0.42 ± 0.003 [2.20×] |
| 20g (BO-1648) | CONH-i-Pr | 4'-MeO—C$_6$H$_4$ | 0.14 ± 0.002 | 0.17 ± 0.004 [1.17×] | 0.25 ± 0.008 [1.47×] |
| 18j (BO-1727) | H | Cyclopropane | 0.97 ± 0.07 | 2.31 ± 0.0048 [2.37×] | 2.44 ± 0.01 [2.51×] |
| 19j (BO-1728) | CONHEt | Cyclopropane | 0.17 ± 0.03 | 0.68 ± 0.004 [4.01×] | 0.54 ± 0.008 [3.18×] |
| 20j (BO-1729) | CONH-i-Pr | Cyclopropane | 0.10 ± 0.01 | 0.73 ± 0.013 [7.30×] | 0.90 ± 0.011 [9.00×] |

[a]CCRF-CEM/Taxol and CCRF-CEM/VBL are subcell lines of CCRF-CEM cells that are 330-fold resistant to Taxol, and 680-fold resistant to Vinblastine, respectively, when comparing with the IC$_{50}$ of the parent cell line.
[b]Numbers in the brackets are fold of cross-resistant determined by comparison with the corresponding IC$_{50}$ of the parent cell line.

TABLE 6

The cytotoxicity of newly synthesized 2,3-bis(hydroxymethyl)benzo-[d]pyrrolo[2,1-b]thiazole and their bis(alkylcarbamate) derivatives against human solid tumors: breast carcinoma MX-1 and colon carcinoma HCT-116, prostate PC3, lung H1299, oral OECM1, and glioma U87.

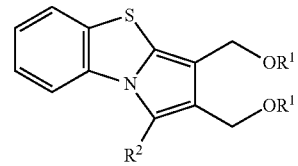

| Compd. | IC$_{50}$ (μM) | | | | | |
|---|---|---|---|---|---|---|
| | MX-1 | HCT-116 | H1299 | PC3 | OECM-1 | U87 |
| 18a (BO-1595) | 7.10 ± 0.037 | 4.44 ± 0.08 | ND | ND | ND | ND |
| 20a (BO-1652) | 0.13 ± 0.001 | 0.97 ± 0.018 | ND | ND | ND | ND |
| 18b (BO-1592) | 2.77 ± 0.005 | 9.59 ± 0.19 | 9.27 ± 1.69 | 13.78 ± 2.15 | 6.03 ± 1.20 | 15.46 ± 1.31 |
| 19b (BO-1593) | 0.48 ± 0.005 | 0.52 ± 0.025 | 13.55 ± 2.03 | 23.70 ± 3.05 | 11.47 ± 2.63 | 29.24 ± 2.63 |
| 20b (BO-1597) | 0.62 ± 0.014 | 0.35 ± 0.010 | 33.03 ± 3.20 | 24.19 ± 4.17 | 11.89 ± 2.90 | 53.50 ± 9.97 |
| 18c (BO-1582) | 10.40 ± 0.003 | 9.26 ± 0.049 | 12.43 ± 0.44 | 20.41 ± 3.43 | 14.60 ± 1.13 | 20.66 ± 2.26 |
| 19c (BO-1596) | 0.91 ± 0.01 | 0.70 ± 0.008 | 4.33 ± 0.45 | 13.85 ± 3.78 | 11.61 ± 2.84 | 26.01 ± 2.27 |
| 20c (BO-1600) | 1.19 ± 0.004 | 1.70 ± 0.006 | 8.75 ± 0.88 | 13.71 ± 1.28 | 7.54 ± 0.95 | 29.04 ± 4.49 |
| 18d (BO-1601) | ND | ND | 21.35 ± 3.74 | 15.22 ± 1.86 | 8.48 ± 0.67 | 17.36 ± 1.86 |
| 19d (BO-1602) | 1.49 ± 0.04 | 1.10 ± 0.015 | 10.33 ± 1.11 | 19.27 ± 3.44 | 14.60 ± 3.39 | 38.48 ± 7.21 |
| 20d (BO-1635) | 1.00 ± 0.002 | 0.41 ± 0.005 | 30.75 ± 6.92 | 29.56 ± 1.83 | 15.10 ± 1.34 | 74.85 ± 15.69 |
| 18g (BO-1646) | ND | ND | 9.94 ± 1.87 | 8.81 ± 1.20 | 5.00 ± 0.78 | 18.10 ± 3.71 |

TABLE 6-continued

The cytotoxicity of newly synthesized 2,3-bis(hydroxymethyl)benzo-[d]pyrrolo[2,1-b]
thiazole and their bis(alkylcarbamate) derivatives against human solid tumors: breast carcinoma
MX-1 and colon carcinoma HCT-116, prostate PC3, lung H1299, oral OECM1, and glioma U87.

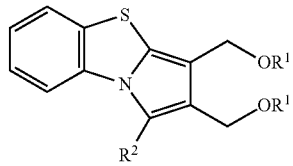

| | | | $IC_{50}$ (μM) | | | |
|---|---|---|---|---|---|---|
| Compd. | MX-1 | HCT-116 | H1299 | PC3 | OECM-1 | U87 |
| 19g (BO-1647) | ND | ND | 8.85 ± 1.53 | 17.90 ± 3.59 | 9.39 ± 1.90 | 29.47 ± 4.86 |
| 20g (BO-1648) | ND | ND | 8.19 ± 1.74 | 17.49 ± 0.80 | 7.23 ± 1.57 | 60.88 ± 13.43 |
| 18j (BO-1727) | ND | ND | 13.32 ± 2.23 | 10.74 ± 2.29 | 7.12 ± 0.95 | 28.70 ± 4.32 |
| 19j (BO-1728) | ND | ND | 20.64 ± 1.89 | 24.19 ± 2.96 | 26.28 ± 4.44 | 74.50 ± 8.70 |
| 20j (BO-1729) | ND | ND | 20.44 ± 1.65 | 13.38 ± 0.84 | 9.67 ± 1.06 | 45.49 ± 6.19 |
| Cisplatin | ND | ND | 16.53 ± 0.90 | 4.71 ± 0.66 | 2.44 ± 0.53 | 54.57 ± 3.33 |

TABLE 7

The cytotoxicity of newly synthesized 2,3- bis(hydroxymethyl)-5H-indolizino[6,7-b]-
indole and their bis(alkylcarbamate) derivatives against human lymphoblastic leukemia (CCRF-
CEM) and solid tumor cell growth in vitro.

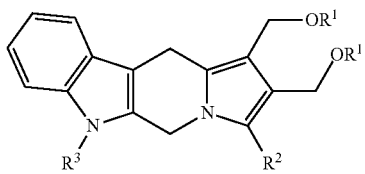

| | | | | $IC_{50}$ (μM) | | | |
|---|---|---|---|---|---|---|---|
| Compd. | CCRF/CEM | MX-1 | HCT-116 | PC3 | H1299 | U87 | OECM1 |
| 33a (BO-1922) | 0.042 ± 0.0003 | 0.22 ± 0.019 | 0.12 ± 0.001 | ND | 3.96 ± 1.79 | 6.54 ± 2.16 | ND |
| 33b (BO-1972) | 0.10 ± 0.002 | ND | ND | 2.66 ± 0.47 | 2.97 ± 0.55 | 6.26 ± 1.43 | 1.17 ± 0.89 |
| 33c (BO-1950) | 0.29 ± 0.003 | ND | ND | 4.52 ± 1.17 | 5.75 ± 0.52 | 11.45 ± 1.80 | 4.17 ± 0.61 |
| 26a (BO-1978) | 0.20 ± 0.002 | ND | ND | 3.32 ± 0.69 | 3.02 ± 0.65 | 9.93 ± 0.88 | 2.11 ± 1.04 |
| 26d (BO-1934) | 4.58 ± 0.378 | 11.28 ± 0.42 | 13.49 ± 0.088 | ND | ND | ND | ND |
| 34a (BO-1923) | 0.040 ± 0.0005 | 0.46 ± 0.001 | 0.24 ± 0.016 | 4.11 ± 1.50 | 6.30 ± 2.80 | 20.12 ± 5.22 | 1.90 ± 0.74 |
| 27d (BO-1935) | 0.35 ± 0.013 | 1.83 ± 0.082 | 1.17 ± 0.009 | ND | ND | ND | ND |
| 27g (BO-1932) | 0.10 ± 0.003 | ND | ND | 8.30 ± 2.24 | 9.80 ± 2.02 | ND | 6.15 ± 1.12 |
| 35a (BO-1924) | 0.033 ± 0.0007 | 0.25 ± 0.002 | 0.089 ± 0.0007 | 73.03 ± 1.29 | ND | 15.35 ± 3.22 | ND |
| 28c (BO-1919) | 0.106 ± 0.004 | ND | ND | ND | 16.88 ± 2.69 | ND | 6.56 ± 1.15 |
| 28d (BO-1936) | 0.437 ± 0.003 | 12.39 ± 0.050 | 3.06 ± 0.067 | ND | ND | ND | ND |
| cis-Pt | ND | ND | ND | 4.71 ± 0.66 | 16.53 ± 0.90 | 54.57 ± 3.33 | 2.44 ± 0.53 |

In Vivo Studies

Figure 4B:
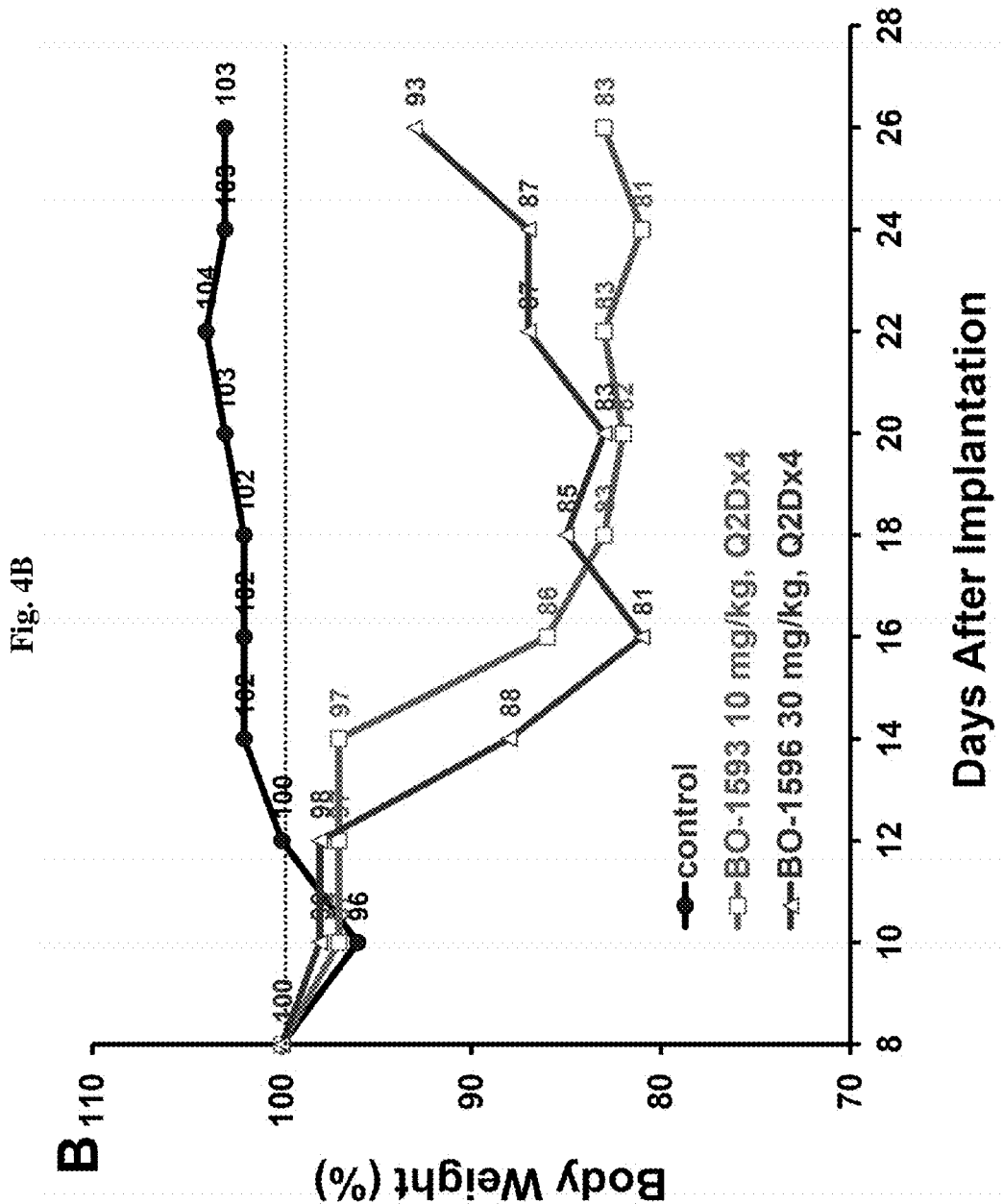
FIG. 4 shows the therapeutic effects of benzo[d]pyrrolo[2,1-b]thiazole derivatives, 19b (BO-1593) and 19c (BO-1596), in nude mice bearing MX-1 human mammary xenograft (i.v. inj., n=3). A: average tumor size changes. B: average body weight changes.
Figure 5A:
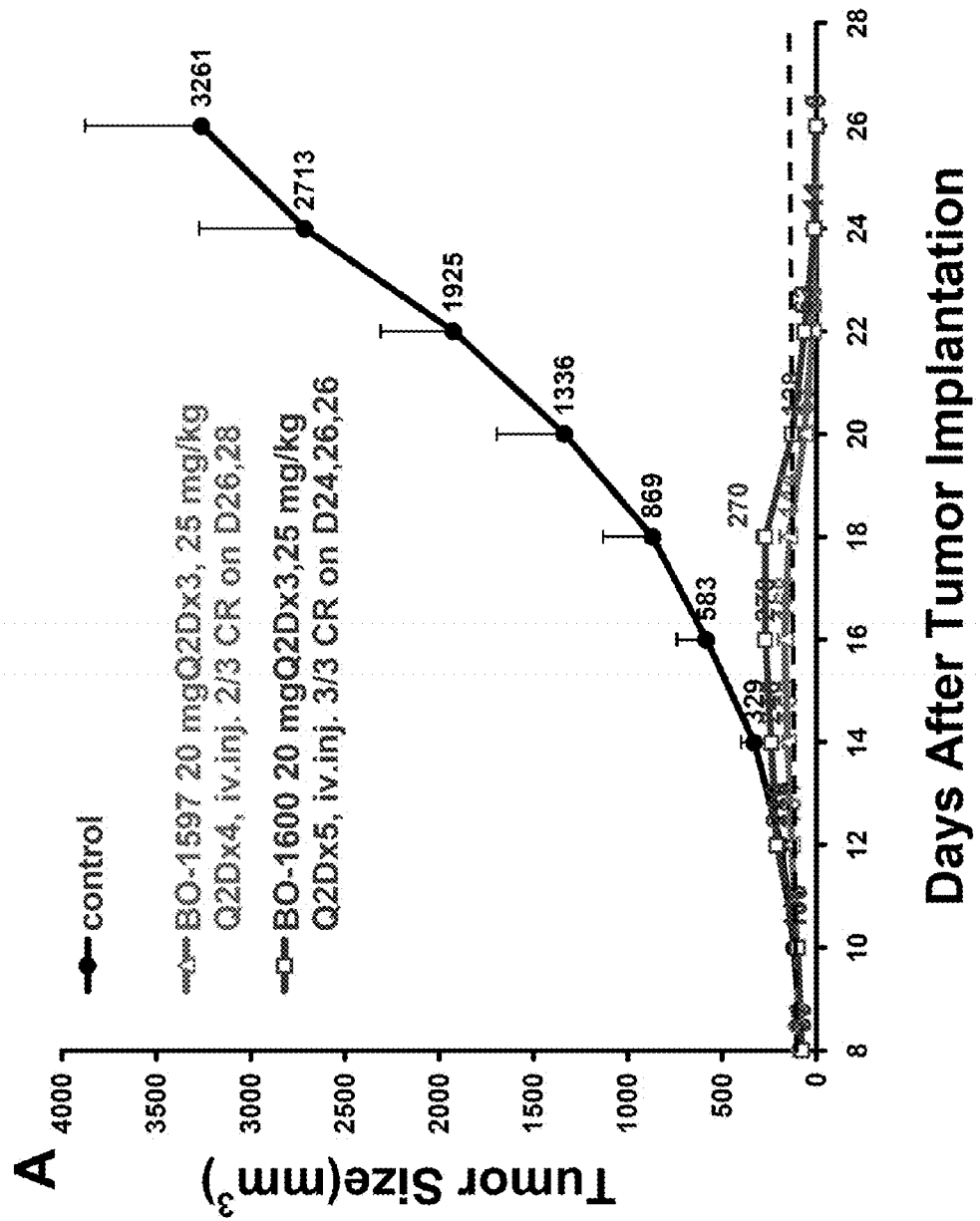
FIG. 5 shows the therapeutic effects of benzo[d]pyrrolo[2,1-b]thiazole derivatives, 20b (BO-1597) and 20c (BO-1600), in nude mice bearing MX-1 human mammary xenograft (i.v. inj., n=3). A: average tumor size changes. B: average body weight changes.
Figure 5B:
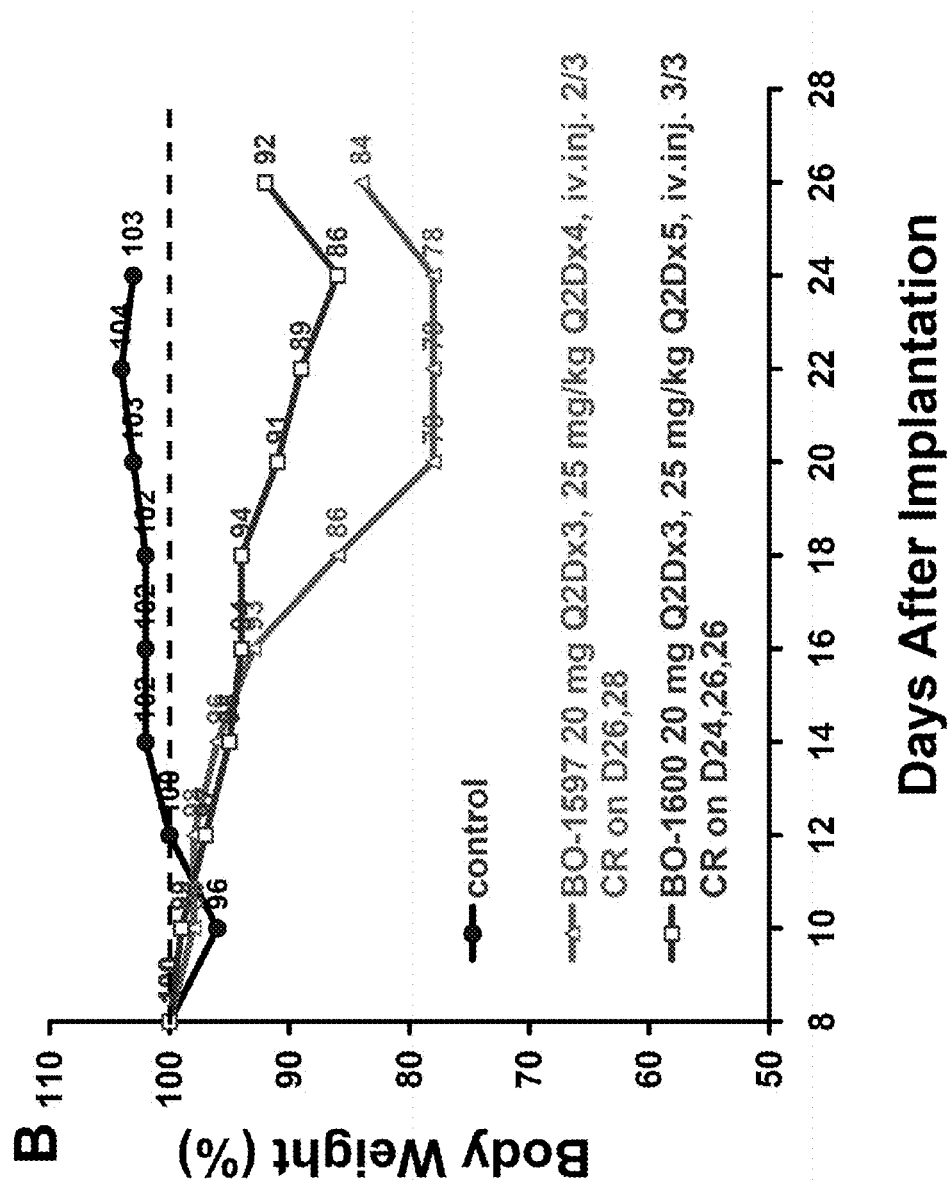

The representative compounds of the newly invented compounds disclosed herein were evaluated for their therapeutic efficacy in nude mice bearing human tumor xenografts. The in vivo therapeutic effects of benzo[d]pyrrolo[2,1-b]-thiazolederivatives are shown in FIG. 4 for compound 19b (BO-1593) and 19c (BO-1596) and FIG. 5 for 20b (BO-1597) and 20c (BO-1600) against human breast cancer MX-1 xenograft in nude mice. It revealed that more than 99% tumor suppression was observed by treating with BO-1593 (10 mg/kg, Q2D×4) or BO-1596 (30 mg/kg, Q2D×4) via intravenous injection (iv. inj.) (FIG. 4A). Remarkably, we found that complete tumor remission (CR) was observed in two out of three mice on D26 and 28 when mice were treated with BO-1597 (20 mg/kg, Q2D×3 and then 25 mg/kg, Q2D×4, iv. inj.). In another experiment, we found complete tumor remission in all three tested mice, when they were treated with BO-1600 (20 mg/kg, Q2D×3 and then 25 mg/kg, Q2D×5) on D24, 26, and 26 (FIG. 5A).

Figure 6B:
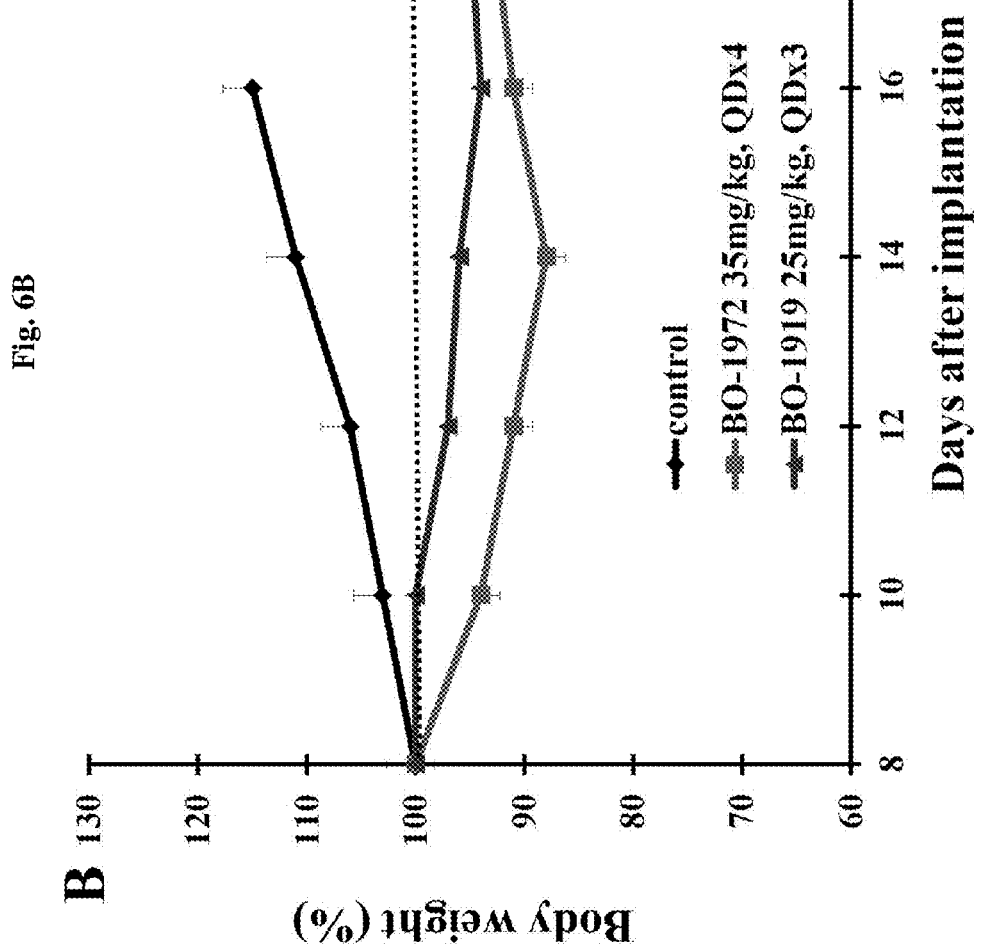
FIG. 6 shows the therapeutic effects of indolizino[6,7-b]indole derivatives, 28c (BO-1919) and 33b (BO-1972), in nude mice bearing MX-1 human mammary xenograft (i.v. inj., n=4). A: average tumor size changes. B: average body weight changes.
Figure 7A:
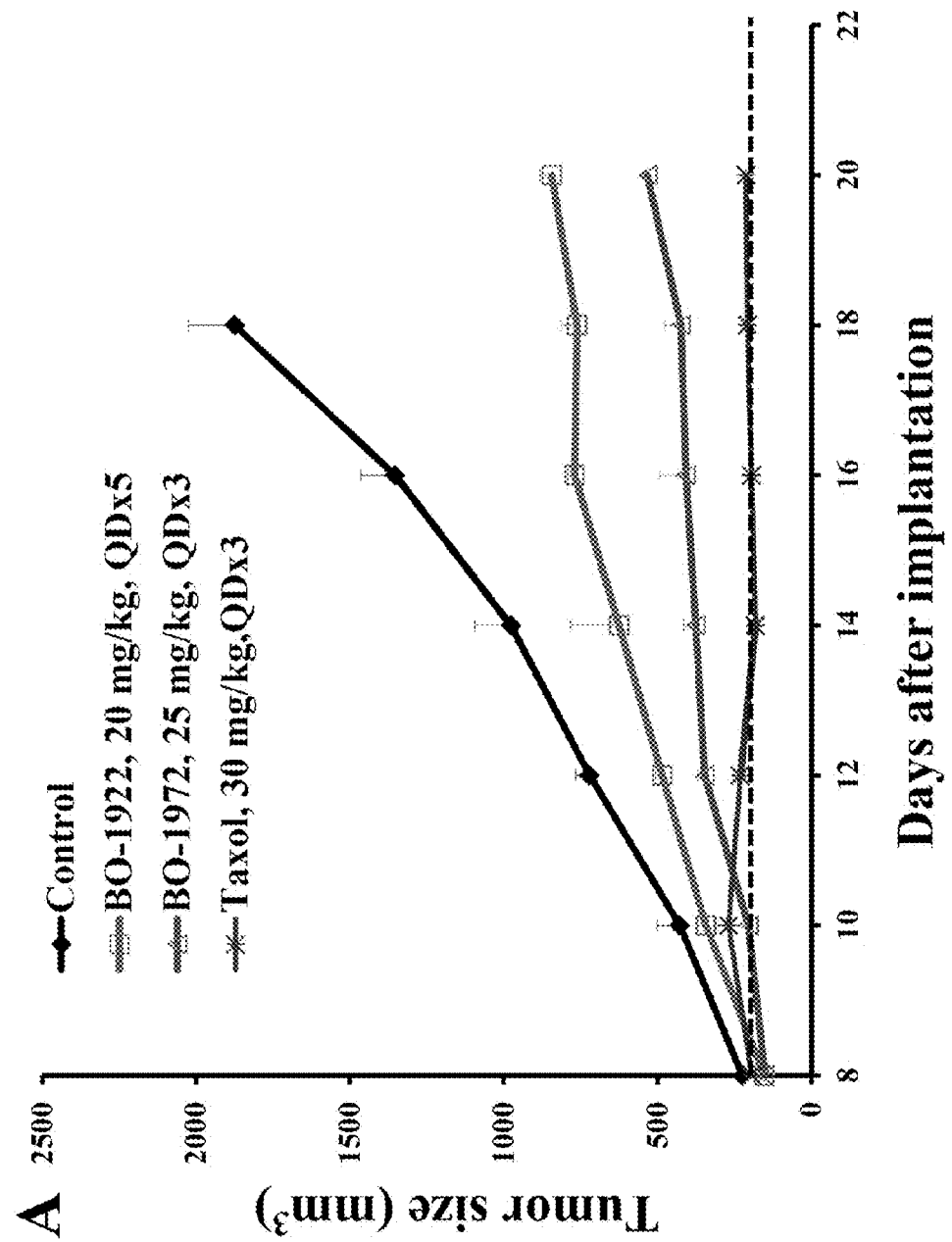
FIG. 7 shows the therapeutic effects of indolizino[6,7-b]indole derivatives, 33a (BO-1922) and 33b (BO-1972), in nude mice bearing human lung cancer A549 xenograft (i.v. inj., n=4). A: average tumor size changes. B: average body weight changes.
Figure 7B:
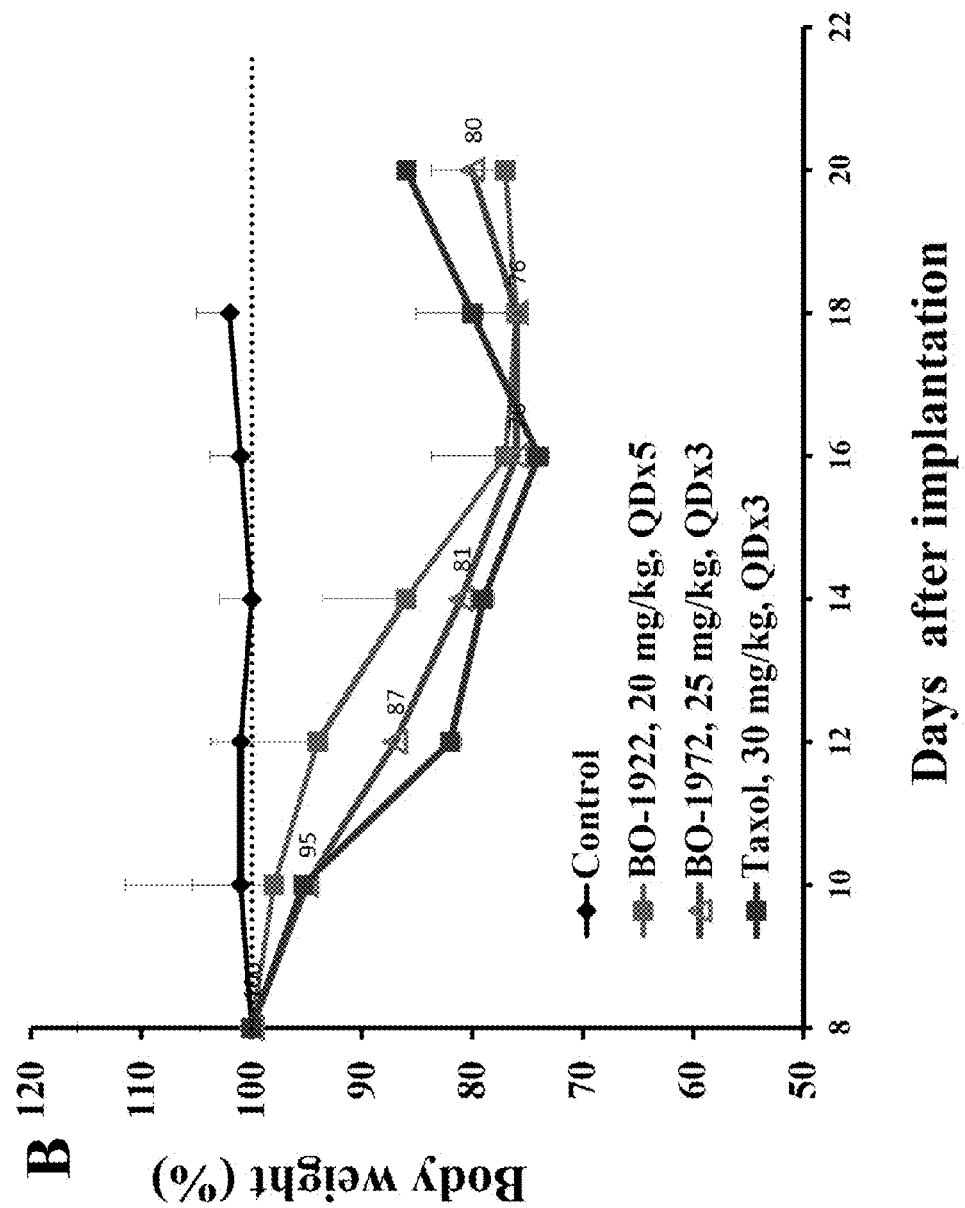

We also have evaluated the therapeutic effects of indolizino [6,7-b]indole derivatives. As shown in FIG. 6, CR was achieved when nude mice bearing MX-1 human mammary xenograft were treated with 28c (BO-1919) and 33b (BO-1972). Additionally, we have evaluated the antitumor activity of 33a (BO-1922) and 33b (BO-1972) in nude mice bearing human lung cancer A549 xenograft and compared that with Taxol.

DNA Cross-Linking Study

Figure 8:
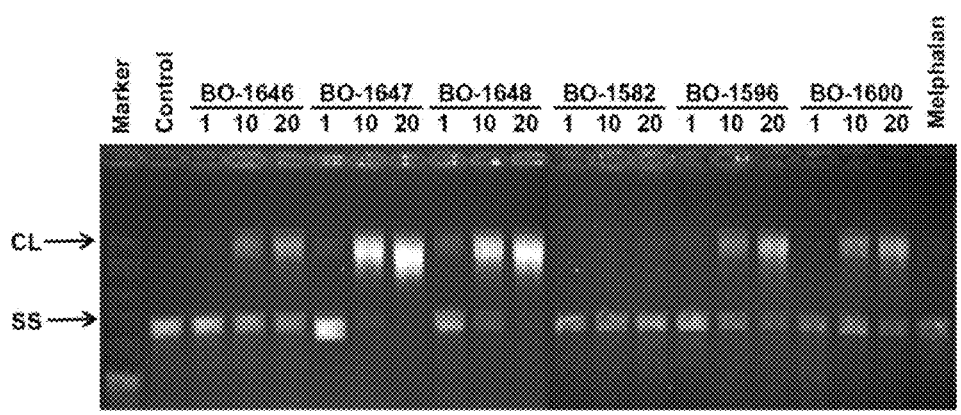
FIG. 8. Representative DNA cross-linking gel shift assay for bis(hydroxymethyl) derivatives of benzo[d]pyrrolo[2,1-b]thiazolederivatives [18g (BO-1646) and 18c (BO-1582)] and their corresponding bis(alkylcarbamate) derivatives [19g (BO-1647), 20g (BO-1648), 19c (BO-1596) and 20c (BO-1600)] at various concentrations as indicated. Melphalan (1, 10, and 20 μM) was used as a positive control.

We have studied the capability of DNA cross-linking (linearized pBR322DNA) by bis(hydroxymethyl) derivatives of benzo[d]pyrrolo[2,1-b]thiazole derivatives [18g(BO-1646) and 18c (BO-1582)] (Formula I) and their corresponding bis(alkylcarbamate) derivatives [19g(BO-1647), 20g (BO- 1648), 19c (BO-1596) and 20c (BO-1600)] (Formula II) at various concentrations as indicated (1, 10, and 20 µM) using alkaline agarose gel shifting assay. Melphalan was used as the positive control. As shown in FIG. 8, all tested compounds are able to bind covalently (interstrand cross-linking) with DNA, suggesting that DNA cross-linking may be the main mechanism of action for these agents.

Biological Methods

Tumor and Cell Lines

Human colon carcinoma HCT-116 cells and human prostate adenocarcinoma PC-3 cells were obtained from American Type Culture Collection (ATCC, Rockville, Md.). Human mammary carcinoma (MX-1) tumor cells were obtained from MSKCC cell bank. The CCRF-CEM human lymphoblastic leukemia cells and their vinblastine resistant subline (CCRF-CEM/VBL, 680-fold resistance in vitro) were obtained from Dr. William Beck of the University of Illinois, Chicago, and CCRF-CEM/Taxol (330-fold resistance in vitro). Resistant cells CCRF-CEM/taxol were produced by exposing the parent cells to increasing sublethal concentration ($IC_{50}$-$IC_{90}$) of paclitaxel for six months.

Prostate cancer PC3, non-small cell lung carcinoma cells H1299, and human glioma cells U87 were purchased from the American Type Culture Collection (Rockville, Md.). OECM-1 (human gingival squamous cell carcinoma cells) was obtained from Dr C.-L. Meng (National Defense Medical College, Taiwan).[22]

Cytotoxicity Assays

In preparation for in vitro cytotoxicity assays, cells were cultured at an initial density $2$–$5 \times 10^4$ cells per milliliter. They were maintained in a 5% $CO_2$-humidified atmosphere at 37° C. in RPMI medium 1640 (GIBCO/BRL) containing penicillin (100 units/mL), streptomycin (100 µg/mL, GIBCO/BRL), and 5% heat-inactivated FBS. For cells grown in suspension (such as CCRF-CEM and its sublines), cytotoxicity was measured, by using XTT microculture method[23] in 96-well microtiter plates.

The cytotoxic effects of the newly synthesized compounds were determined in T-cell acute lymphocytic leukemia (CCRF-CEM) and their resistant subcell lines (CCRF-CEM/Taxol and CCRF-CEM/VBL) by the XTT assay[24] and human solid tumor cells (i.e. breast carcinoma MX-1 and colon carcinoma HCT-116) by the SRB assay[25] in a 72 h incubation using a microplate spectrophotometer as described previously.[25] After the addition of phenazine methosulfate-XTT solution, incubated at 37° C. for 6 h and absorbance at 450 and 630 nm was detected on a microplate reader (EL 340). The cytotoxicity of the newly synthesized compounds against non-small cell lung carcinoma H1299, prostate cancer PC3, oral cancer OECM-1 and glioma U87 were determined by the Alamar blue assay[26] in a 72 h incubation using a microplate spectrophotometer as described previously. After the addition of alamar blue solution, it was incubated at 37° C. for 6 h. Absorbance at 570 and 600 nm was detected on a microplate reader. $IC_{50}$ values were determined from dose-effect relationship at six or seven concentrations of each drug using the CompuSyn software by Chou and Martin[27] based on the median-effect principle and plot.[28,29] Ranges given for Cisplatin were mean±SE (n=4).

Animals

Athymic nude mice bearing the nu/nu gene were obtained from NCI, Frederick, Md. and used for all human tumor xenografts. Male nude mice, 6 weeks or older, weighing 20-24 g or more were used. Compounds were administered via the tail vein for i.v. injection or infusion as described previously.[26] A typical formulation for chemotherapeutic studies for each drug was dissolved in DSMO to make a 25 mg/ml fresh solution, 0.4 ml of this solution was mixed with 0.3 ml of Tween 80, plus 1.3 ml to make 2 ml of 5 mg/ml solution. Bolus injection volume was 0.1-0.2 ml per mouse. Tumor volume was assessed by measuring length×width× height (or width) by using a caliper. For tumor-bearing nude mice during the course of the experiment, the body weight refers to total weight minus the weight of the tumor. All animal studies were conducted in accordance with the guidelines for the National Institute of Health Guide for the Care and Use of Animals and the protocol approved by the Institutional Animal Care and Use Committee.

Alkaline Agarose Gel Shift Assay.

Formation of DNA cross-linking was analyzed by alkaline agarose gel electrophoresis assay. In brief, purified pEGFP-N1 plasmid DNA (1500 ng) was mixed with various concentrations (1-20 µM) of the tested compounds in 40 µL binding buffer (3 mM sodium chloride/1 mM sodium phosphate, pH 7.4, and 1 mM EDTA). The reaction mixture was incubated at 37° C. for 2 h. At the end of reaction, the plasmid DNA was linearized by digestion with BamHI and followed by precipitation with ethanol. The DNA pellets were dissolved and denatured in alkaline buffer (0.5 N NaOH-10 mM EDTA). An aliquot of 20 µL of DNA solution (1000 ng) was mixed with 4 µL of 6× alkaline loading dye and then electrophoretically resolved on a 0.8% alkaline agarose gel with NaOH-EDTA buffer at 4° C. The electrophoresis was carried out at 18 V for 22 h. After staining the gels with an ethidium bromide solution, the DNA was then visualized under UV light.

The invention is not limited by the embodiments described above which are presented as examples only but can be modified in various ways within the scope of protection defined by the appended patent claims.

REFERENCE

1. Elliot, W. L.; Fry, D. W.; Anderson, W. K.; Nelson, J. M.; Hook, K. E.; Hawkins, P. A.; Leopold, W. R. In vivo and in vitro evaluation of the alkylating agent carmethizole. *Cancer Res.* 1991, 51, 4581-4587.
2. Weidner, M. F.; Sigurdsson, S. T.; Hopkins, P. B. Sequence preferences of DNA interstrand cross-linking agents: dG-to-dG cross-linking at 5'-CG by structurally simplified analogs of mitomycin C. *Biochemistry,* 1990, 29, 9225-9233.
3. Woo, J.; Sigurdsson, S. T.; Hopkins, P. B. DNA interstrand cross-linking reactions of pyrrole-derived, bifunctional electrophiles: evidence for a common target site in DNA. *J. Am. Chem. Soc.* 1993, 115, 3407-3415.
4. Andeson, W. K.; New, J. S.; Corey, P. F. Tumor inhibitory agents. Bis(N-alkylcarbamate) derivatives of 2,3-dihydro-5-(3',4'-dichlorophenyl)-6,7-bis(hydroxymethyl)-1H-pyrrolizine. *Arzneim. Forsch.* 1980, 30, 765-768.
5. Anderson, W. K.; McPherson, H. L.; New, J. S.; Rick, A. C. Synthesis and murine antineoplastic activity of bis[carbamoyloxymethyl] derivatives of pyrrolo[2,1-a]isoquinoline. *J. Med. Chem.* 1984, 27, 1321-1325.
6. Anderson, W. K. Activity of bis-carbamoyloxymethyl derivatives of pyrroles and pyrrolizines against human tumor xenografts in nude mice. *Cancer Res.* 1982, 42, 2168-2170.
7. Kakadiya R.; Dong, H.; Lee P.-C.; Kapuriya, N.; Zhang, X.; Chou, T.-C.; Lee, T.-C.; Kapuriya, K.; Shah, A.; Su, T.-L. Potent antitumor bifunctional DNA alkylating agents, synthesis and biological activities of 3a-aza-cyclopenta[a]indenes. *Bioorg. Med. Chem.* 2009, 17, 5614-5626.
8. Lee P.-C.; Kakadiya R.; Su, T.-L.; Lee, T.-C. Combination of bifunctional alkylating agent and arsenic trioxide synergistically suppresses the growth of drug-resistant tumor cells. *Neoplasia.* 2010, 12, 376-387.
9. Chaniyara, R.; Kapuriya, N.; Dong, H.; Lee, P.-C.; Suman, S.; Marvania, B.; Chou, T.-C.; Lee, T.-C.; Kakadiya, R.; Shah, A.; Su, T.-L. Novel bifunctional alkylating agents, 5,10-dihydropyrrolo[1,2-b]isoquinoline derivatives, synthesis and biological activity. *Boorg. Med. Chem.* 2010, 19, 1987-1998.
10. Lalezari, I.; Schwartz, E. L. synthesis and antineoplastic activity of 5-aryl-2,3-dihydropyrrolo[2,1-b]thiazole-6,7-dimethanol 6,7-bis(isopropylcarbamates). *J. Med. Chem.* 1988, 31, 1427-1429.
11. Anderson, W. K. Activity of bis-carbamoyloxymethyl derivatives of pyrroles and pyrrolizines against human tumor xenografts in nude mice. *Cancer Res.* 1982, 42, 2168-2170.
12. Pandya, A; Gibson, H. W.; Synthesis and stereochemistry of reissert compounds from benzothiazole. *J. Org. Chem.* 1993, 58, 2851-2855.
13. McEwen, W. E.; Mineo, I. C.; Shen, Y. H. 1,3-Dipolar addition reactions of reinsert compounds *J. Am. Chem. Soc.* 1971, 93, 4479-4484.
14. Deveau, A. M.; Labroli, M. A., Dieckhaus, C. M.; Barthen, M. T.; Smith, K. S.; Macdonald, T. L. The Synthesis of amino-acid functionalized β-carbolines as topoisomerase II inhibitors. *Bioorg. Med. Chem. Lett.* 2001, 11, 1251-1255.
15. Cao, R.; Peng, W.; Wang, Z.; Xu, A. β-Carboline alkaloids: Biochemical and pharmacological functions. *Curr. Med. Chem.* 2007, 14, 479-500.
16. Pandya, A.; Gibson, H. W. Synthesis and stereochemistry of reissert compounds from benzothiazole. *J. Org. Chem.* 1993, 58, 2851-2855.
17. Berrabah, M.; Schmitt, G.; Dinh, N.; Laude, B.; Condensation of 2-cyano-3-paranitrobenzoyl-2,3-dihydrobenzothiazole hydrofluoroborate with alkynes and alkenes *Bull. Soc. Chim. Belg.* 1991, 100, 613-616.
18. Lin, N.; Zhao, M.; Wang, C.; Peng, S. Synthesis and antithrombotic activity of carbolinecarboxyl RGD sequence. *Bioorg. Med. Chem.,* 2002, 12, 585-587.
19. Saxena, A. K.; Pandey, S. K.; Tripathi R. C.; Raghubir, R. Synthesis, Molecular Modeling and QSAR Studies in Chiral 2,3-disubstituted-1,2,3,4-tetrahydro-9H-pyrido(3,4-b)indoles as Potential Modulators of Opioid Antinociceptiony. *Bioorg. Med. Chem.* 2001, 9, 1559-1570.
20. Hershenson, F. M., Synthesis of ring-fused pyrrole. I. 1,3-dipolar cycloaddition reactions of munchnone derivatives obtained from tetrahydro-β-carboline-3-and-1-carboxylic acids. *J. Org. Chem.,* 1972, 37, 3111-3113.
21. Uff, B. C.; Ho, Y.-P.; Brown, D. S.; Fisher, I.; Popp, F. D.; Kant, J. Reissert compound formation with fused five-membered ring heterocycles. *J. Chem. Res. Miniprint,* 1989, 11, 2652-2681.
22. Lai, K.-C.; Chang, K.-W.; Liu, C.-J.; Kao, S.-Y.; Lee, T.-C. IFN-induced protein with tetratricopeptide repeats 2 inhibits migration activity and increases survival of oral squamous cell carcinoma. *Mol. Cancer. Res.* 2008, 6, 1431-1439.
23. Scudiero, D. A.; Shoemaker, R. H.; Paull, K. D.; Monks, A.; Tierney, S.; Nofziger, T. H.; Currens, M. J.; Seniff, D.; Boyd, M. R. Evaluation of soluble tetrazolium/formazan assay for cell growth and drug sensitivity in culture using human and other tumor cell lines. *Cancer Res.* 1988, 48, 4827-4833.
24. Skehan, P.; Storeng, R.; Scudiero, D.; Monks, A.; McMahon, J.; Vistica, D.; Warren, J. T.; Bokesch, H.; Kenny, S.; Boyd, M. R. New colorimetric cytotoxicity assay for anticancer-drug screening. *J. Natl. Cancer Inst.* 1990, 82, 1107-1112.
25. Chou, T.-C.; O'Connor, O. A.; Tong, W. P.; Guan, Y.; Zhang, Z.-G.; Stachel, S. J.; Lee, C.; Danishefsky, S. J. The Synthesis, discovery and development of a highly promising class of microtubule stabilization agents: Curative effects of desoxyepothilones B and F against human tumor xenografts in nude mice. *Proc. Natl. Acad. Sci. USA* 2001, 98, 8113-8118.
26. Al-Nasiry, S.; Hanssens, M.; Luyten, C.; Pijnenborn, R. The use of alamarblue assay for quantitative analysis of viability, migration and invasion of choriocarcinoma cells. *Hum Reprod.* 2007, 22, 1304-1309.
27. Chou, T.-C.; Martin, N. CompuSyn for drug combinations: PC Software and user's guide: A computer program for quantitation of synergism and antagonism in drug combinations, and the determination of $IC_{50}$ and $ED_{50}$ and $LD_{50}$ Values. ComboSyn, Inc., Paramus, N.J., 2005.
28. Chou, T.-C.; Talalay, P. Quantitative analysis of dose-effect relationships: The combined effects of multiple drugs or enzyme inhibitors. *Adv. Enzyme Regul.* 1984, 22, 27-55.
29. Chou, T.-C. Theoretical basis, experimental design and computerized simulation of synergism and antagonism in drug combination studies. *Pharmacol. Rev.* 2006, 58, 621-681.

We claim:

1. The compound of Formula III:

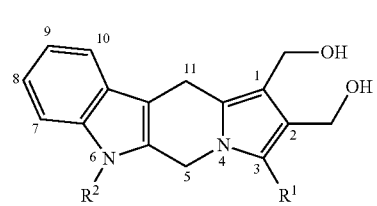

Formula III wherein:
R$^1$ is selected from the group consisting of hydrogen, a $C_1$-$C_5$ linear, branched or cyclic alkyl group, an unsubstituted or substituted aryl, and an unsubstituted or substituted benzyl group; and R$^2$ is selected from the group consisting of hydrogen, a C1-C5 linear, branched or cyclic alkyl group, an unsubstituted or substituted benzyl, an acyl (R$^a$CO), a methansulfonyl (Me$_2$SO$_2$), a toluenesulfonyl MeC$_6$H$_4$SO$_2$); wherein R$^a$ is a C1-C5 linear, branched or cyclic alkyl group, an unsubstituted or substituted aryl, and an unsubstituted or substituted benzyl.

2. The compound of claim 1 wherein the unsubstituted or substituted aryl group is selected from the group consisting of unsubstituted or substituted phenyl, naphthyl, pyrenyl, anthryl, and phenanthryl, furyl, pyrrolyl, thienyl, oxazoyl, imidazoyl, thiazoyl, pyridyl, pyrimidinyl, quinazolinyl and indolyl.

3. The compound of claim 1 wherein the substituent of the aryl or benzyl is selected from the group consisting of $C_1$-$C_6$ alkyl, OR$^a$; halo, cyano, nitro, NH$_2$, NHR$^b$, N(R$^b$)$_2$, a $C_3$-$C_6$ cyclic alkylamino group, a methylenedioxy and ethylenedioxy group; wherein R$^a$ is hydrogen or $C_1$-$C_{10}$ alkyl, and R$^b$ is hydrogen or $C_1$-$C_{10}$ alkyl.

4. The compound of claim 1 selected from the group consisting of (3-(phenyl)-6-methyl-6,11-dihydro-5H-indolizino[6,7-b]indole-1,2-diyl)dimethanol;

(3-(4-Fluorophenyl)-6-methyl-6,11-dihydro-5H-indolizino[6,7-b]indole-1,2-diyl)dimethanol;

3-(4-Chlorophenyl)-6-methyl-6,11-dihydro-5H-indolizino[6,7-b]indole-1,2-diyl)dimethanol;

(3-(3,4-Difluorophenyl)-6-methyl-6,11-dihydro-5H-indolizino[6,7-b]indole-1,2-diyl)dimethanol;

[6-Methyl-3-phenyl-6,11-dihydro-5H-indolizino[6,7-b]indole-1,2-diyl]bis(methylene) bis(ethylcarbamate);

[3-(4-Fluorophenyl)-6-methyl-6,11-dihydro-5H-indolizino[6,7-b]indole-1,2-diyl]bis(methylene) bis(ethylcarbamate);

[3-(4-Chlorophenyl)-6-methyl-6,11-dihydro-5H-indolizino[6,7-b]indole-1,2-diyl]bis(methylene) bis(ethylcarbamate); and

[3-(4-Difluorophenyl)-6-methyl-6,11-dihydro-5H-indolizino[6,7-b]indole-1,2-diyl]bis(methylen) bis(ethylcarbamate).

5. The compound of Formula IV

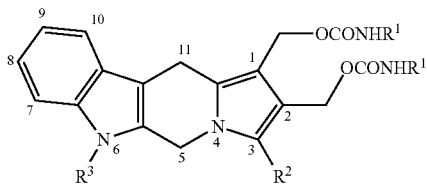

Formula IV wherein:

$R^1$ and $R^2$ are the same or different, and are hydrogen, a $C_1$-$C_5$ linear, branched or cyclic alkyl group, an unsubstituted or substituted aryl or an unsubstituted or substituted benzyl group; and $R^3$ is selected from the group consisting of hydrogen, a C1-C5 linear, branched or cyclic alkyl group, an unsubstituted or substituted benzyl, an acyl ($R^aCO$), a methansulfonyl ($Me_2SO_2$), and a toluenesulfonyl ($MeC_6H_4SO_2$); wherein $R^a$ is a C1-C5 linear, branched or cyclic alkyl group, an unsubstituted or substituted aryl, and an unsubstituted or substituted benzyl.

6. The compound of claim 5 wherein the unsubstituted or substituted aryl group is selected from the group consisting of unsubstituted or substituted phenyl, naphthyl, pyrenyl, anthryl, and phenanthryl, furyl, pyrrolyl, thienyl, oxazoyl, imidazoyl, thiazoyl, pyridyl, pyrimidinyl, quinazolinyl and indolyl.

7. The compound of claim 5 wherein the substituent of the aryl or benzyl is selected from the group consisting of $C_1$-$C_6$ alkyl, $OR^a$; halo, cyano, nitro, $NH_2$, $NHR^b$, $N(R^b)_2$, a $C_3$-$C_6$ cyclic alkylamino group, a methylenedioxy, and ethylenedioxy group; wherein $R^a$ is hydrogen or $C_1$-$C_{10}$ alkyl, and $R^b$ is hydrogen or $C_1$-$C_{10}$ alkyl.

8. The compound of claim 5 selected from the group consisting of

[6-Methyl-3-phenyl-6,11-dihydro-5H-indolizino[6,7-b]indole-1,2-diyl]bis(methylene)bis(iso propylcarbamate);

[3-(4-Fluorophenyl)-6-methyl-6,11-dihydro-5H-indolizino[6,7-b]indole-1,2-diyl]bis(methylene) (isopropylcarbamate);

[3-(4-Chlorophenyl)-6-methyl-6,11-dihydro-5H-indolizino[6,7-b]indole-1,2-diyl]bis(methylene) (isopropylcarbamate); and

[3-(3,4-Difluorophenyl)-6-methyl-6,11-dihydro-5H-indolizino[6,7-b]indole-1,2-diyl]bis(methylene) (isopropylcarbamate).

* * * * *